(12) United States Patent
Hoyos et al.

(10) Patent No.: US 9,869,618 B2
(45) Date of Patent: *Jan. 16, 2018

(54) METHOD OF FORMING AN AGGREGATE OF OBJECTS

(75) Inventors: Mauricio Hoyos, Creteil (FR); Luz Angelica Castro Camacho, Paris (FR)

(73) Assignees: CENTRE NATIONAL DE LA RECHERCHE SCIENTIFIQUE, Paris (FR); ECOLE SUPERIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 563 days.

This patent is subject to a terminal disclaimer.

(21) Appl. No.: 14/380,111

(22) PCT Filed: Feb. 27, 2012

(86) PCT No.: PCT/IB2012/000511
§ 371 (c)(1),
(2), (4) Date: Apr. 22, 2015

(87) PCT Pub. No.: WO2013/128224
PCT Pub. Date: Sep. 6, 2013

(65) Prior Publication Data
US 2015/0285719 A1    Oct. 8, 2015

(51) Int. Cl.
*G01N 1/40* (2006.01)
*C12N 5/00* (2006.01)

(52) U.S. Cl.
CPC ......... *G01N 1/4077* (2013.01); *C12N 5/0062* (2013.01); *C12N 2521/10* (2013.01); *G01N 2001/4094* (2013.01)

(58) Field of Classification Search
CPC ............ C12N 2521/10; C12N 2513/00; C12N 5/0062; C12N 5/0693; G01H 17/00;
(Continued)

(56) References Cited

U.S. PATENT DOCUMENTS

| 4,877,516 A * | 10/1989 | Schram | B01D 21/283 209/155 |
| 6,216,538 B1 * | 4/2001 | Yasuda | B01D 21/283 210/748.05 |

(Continued)

FOREIGN PATENT DOCUMENTS

WO     WO 2010/135044 A1    11/2010

OTHER PUBLICATIONS

Bazou et al., "Physical Environment of 2-D Animal Cell Aggregates Formed in a Short Pathlength Ultrasound Standing Wave Trap," *Ultrasound in Medicine and Biology*, Mar. 2005, vol. 31, No. 3, pp. 423-430.

(Continued)

*Primary Examiner* — Laura Martin
*Assistant Examiner* — Rose M Miller
(74) *Attorney, Agent, or Firm* — Oliff PLC

(57) ABSTRACT

A method of forming an aggregate of objects in a channel including a liquid, the method including: a) providing objects in at least a region of the channel, and b) forming an aggregate of the objects by submitting them to a modulated pulsed acoustic field, wherein the modulated pulsed acoustic field applied at step b) is modulated in amplitude.

26 Claims, 14 Drawing Sheets

(58) Field of Classification Search
CPC ............... B01D 21/28; Y10T 137/0324; Y10T 137/206; G01N 15/1459; G01N 15/06; G01N 15/14; G01N 1/40; G01N 2001/4094; G01N 2001/4077; G01N 2015/1413; G01N 2015/142; G01N 2015/1081; G01N 2018/1087; G01N 2015/1093
USPC .............................................. 73/570.5, 61.75
See application file for complete search history.

(56) References Cited

U.S. PATENT DOCUMENTS

| 9,170,186 | B2* | 10/2015 | Hoyos | G01N 15/06 |
| 2008/0067128 | A1 | 3/2008 | Hoyos et al. | |
| 2011/0278218 | A1* | 11/2011 | Dionne | B01D 17/04 |
| | | | | 210/523 |
| 2014/0011240 | A1* | 1/2014 | Lipkens | B01D 21/28 |
| | | | | 435/71.1 |

OTHER PUBLICATIONS

Hultström et al., "Proliferation and Viability of Adherent Cells Manipulated by Standing-Wave Ultrasound in a Microfluidic Chip," *Ultrasound in Medicine and Biology*, Dec. 2006, vol. 33, No. 1, pp. 145-151.

Zhang et al., "Rapid Concentration of Particle and Bioparticle Suspension Based on Surface Acoustic Wave," *Applied Acoustics*, Aug. 2009, vol. 70, No. 8, pp. 1137-1142.

Glynne-Jones et al., "Mode-Switching: A New Technique for Electronically Varying the Agglomeration Position in an Acoustic Particle Manipulator," *Ultrasonics*, Jan. 2010, vol. 50, No. 1, pp. 68-75.

Bazou et al., "Controlled Cell Aggregation in a Pulsed Acoustic Field," *Ultrasonics*, Jan. 2012, vol. 52, No. 7, pp. 842-850.

International Search Report issued in International Application No. PCT/IB2012/000511 dated Oct. 17, 2012.

Written Opinion of the International Searching Authority issued in International Application No. PCT/IB2012/000511 dated Oct. 17, 2012.

* cited by examiner

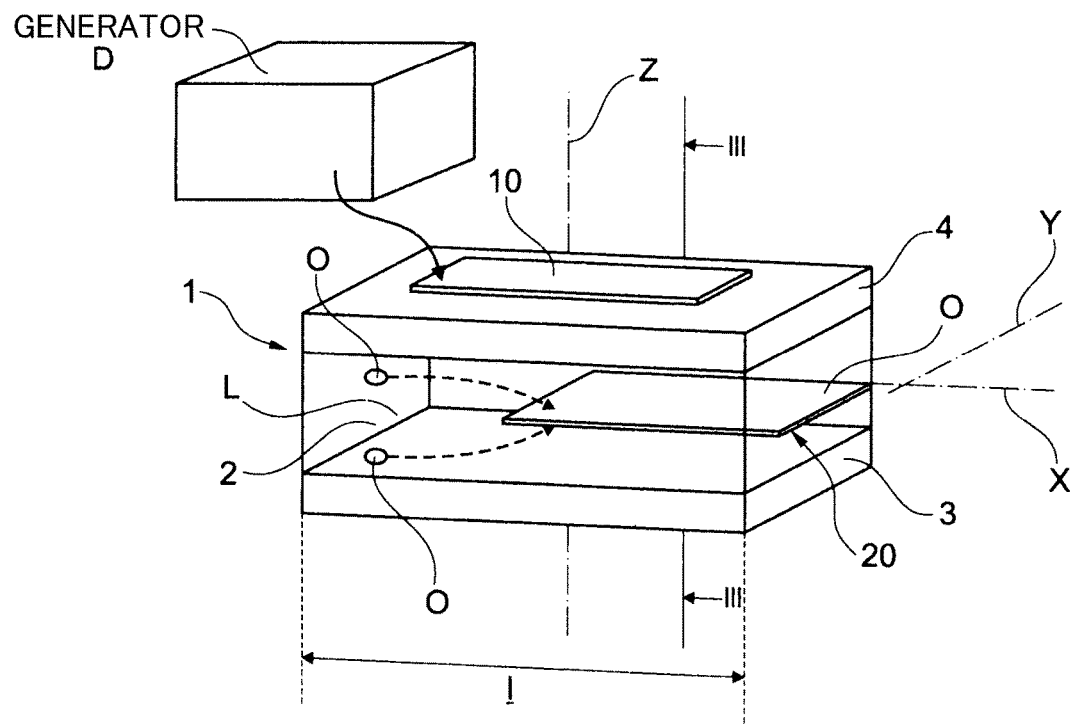
Fig. 1
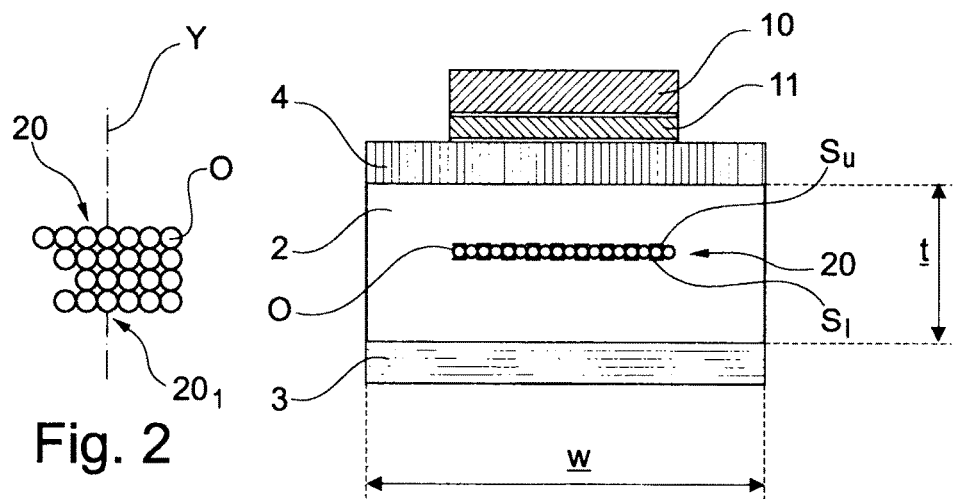
Fig. 2
Fig. 3

METHOD OF FORMING AN AGGREGATE OF OBJECTS

The present invention relates to methods of forming an aggregate of objects in a channel comprising a liquid.

BACKGROUND

Cell manipulation techniques are important in many areas of research including cell biology, molecular genetics, biotechnological production, clinical diagnostics and therapeutics. Physical methods of manipulating suspended cells at single-particle microscopic resolution include hydrodynamic, optical, dielectrophoretic, magnetic and ultrasonic cell trapping.

Of the above-mentioned methods, ultrasound trapping has been less extensively exploited. Compared to other methods, ultrasonic cell manipulation is an inexpensive non-contact technique that allows simultaneous and synchronous manipulation of a large number of cells in a very short time. It is simple in both set-up and operation, and is non-invasive, chemically inert (non-toxic) and physically non-destructive. Taking into account its high efficiency and reliability and the fact that it can be used with the majority of cell types, this technique holds great promise in cell manipulation techniques for a variety of applications.

Forces acting on particles in an acoustic resonator have been studied under different conditions and for different goals. The origin of acoustic forces generated by ultrasonic standing waves has been extensively exploited. Depending on the experimental conditions, some of those forces can be generated and quantified. The most studied acoustic force is the PRF (primary radiation force), which is the force generated by an ultrasonic standing wave occurring between the walls of a resonator. In the case of a closed fluid-filled chamber, resonance is obtained when its thickness is equal to: $w=N\lambda/2$ where N is the number of nodes in the chamber and $\lambda$ is the ultrasound wavelength. The acoustic force $F_{ac}$ drives particles towards the nodes or antinodes depending on their acoustic properties. $F_{ac}=Vk\tilde{A}<E_{ac}>\sin(2kx)$, where V is the particle volume, $k=2\pi/\lambda$ is the wave number, $\tilde{A}=[3(\rho_p-\rho_f)/(2\rho_p+\rho_f)-(c_p^2\rho_p/c_f^2\rho_f)]$ is the acoustic contrast factor, where $c_p$ and $c_f$ are the sound speeds of the particles and the fluid respectively, and $<E_{ac}>$ is the average acoustic energy density. It is well known that the PRF appears as a second order of the Navier-Stokes equation. The order of magnitude of the acoustic force is really low (~$10^{-9}$ N) but high enough for influencing micron sized particles, cells, lipids or even bacteria.

A number of other primary and secondary acoustic forces have also been described, namely: the primary and secondary Bjerknes forces, the secondary interparticle force and the force generated by the transversal component of the PRF; the latter is considered to be the governing force influencing the aggregation process. Several reports have demonstrated that all of the forces mentioned above are at least two orders of magnitude smaller than the axial component of the primary force. Nevertheless, when particles reach the nodal plane the axial net force is zero, thus unveiling the transversal forces leading to the initiation of aggregation.

The aggregation process starts when isolated particles in levitation converge towards a specific point, where the acoustic energy is maximal.

The transversal migration of particles in the nodal plane is due to a complex coupling between forces generated by the non-homogeneity energy field distribution in the chamber and the transversal PRF originated by the imperfections of the resonator (for instance, the parallelism of the resonator walls and the lateral walls vibrations). The particle transversal force is therefore difficult to predict; nevertheless, by measuring the particle transversal velocity the mean transversal force $F_{Tr}$ can be estimated, by considering that it is balanced by the Stokes' force $F_s$, such that: $F_{Tr}-F_s=0$, where $F_s=3\pi\eta d v_{Tr}$, with d being the particle diameter, $\eta$ the dynamic viscosity and $v_{Tr}$ the transversal velocity at the levitation plane. The complexity of the interactions of those forces may make the aggregation process difficult to control. It has been however reported that 2-D or 3-D aggregate configurations can be controlled by the initial concentration of cells.

It has been previously reported the use of an ultrasound standing wave trap (USWT) capable of holding >10,000 cells at the focal plane of a microscope. The USWT is an ultrasound resonator where the acoustic path-length in the cell suspension is a single half wavelength. The resonator has a pressure node plane half way through the cell suspension and parallel to the transducer. The cell trap exploits the fact that cells experience an axial direct acoustic radiation force when in an ultrasound standing wave field. This force drives them towards a node plane. They then move, within that plane, to accumulate at the centre of the field, i.e. at the nodal plane. The USWT has been used to synchronously and rapidly (within 10 s of seconds) form and levitate 2-D and 3-D cell aggregates in suspension away from the influence of solid substrata.

At low cell concentrations ($\leq 5 \times 10^5$ cells/ml), 2-D aggregates may be generated, while at concentrations of $\geq 10^6$ cells/ml, 3-D aggregates may be generated. This presents a relatively narrow particle/cell concentration margin over which 2-D aggregates can be formed. While, undoubtedly 3-D aggregates are more tissue-mimetic, there is still great interest in the 2-D form of the aggregate as this facilitates light microscope resolution of the interaction processes occurring between cells.

In addition, some of the known techniques may not allow a satisfactorily control aggregation mechanism. For example, one way of controlling the aggregation velocity is by tuning the resonance frequency. However, in this case, particle velocities change rapidly at resonance, resulting in poor reproducibility. A need thus exists to obtain a method allowing a more controlled aggregation mechanism.

Another need exists to obtain a method allowing the selective generation of 2-D or 3D aggregates.

The present invention aims to meet one or more of the aforementioned needs.

SUMMARY

According to a first aspect, the present invention provides a method of forming an aggregate of objects in a channel comprising a liquid, said method comprising:
a) providing objects in at least a region of the channel, and
b) forming an aggregate of said objects by submitting them to a modulated pulsed acoustic field, wherein the modulated pulsed acoustic field applied at step b) is modulated in amplitude.

By "aggregate of objects", it is meant a layer of objects satisfying all of the following features:
at least two objects comprised in said layer, in particular at least 10%, better 25%, preferably 50% of the objects comprised in said layer, are in contact, and
said layer presents, on at least a portion of its length, a succession of objects when displacing along at least one of its transverse dimensions.

The obtained aggregates may comprise, in particular consist in, juxtaposed rows of objects. In this case, the aggregates are referred to as 2D-aggregates. A 2D-aggregate may extend in a plane.

In another embodiment, the obtained aggregates comprise a stacking of 2D-aggregates. Such an embodiment is an example of a 3D-aggregate.

An aggregate is different from a line of objects which only extend along an axis. In other words, a line of objects comprises only one object in width, only one object in thickness and a succession of objects along its length. A stacking of a 2D-aggregate and of a line of objects is another example of a 3D-aggregate.

By "pulsed acoustic field modulated in amplitude", it is meant a repetition of a plurality of groups of acoustic wave pulses, said pulses having, among a given group, substantially the same amplitude and frequency, each of said groups being separated by one period having a non-zero duration wherein no acoustic wave is applied or wherein an acoustic wave is applied, said acoustic wave having at least one extremum of the absolute value of its amplitude that is different from the highest amplitude of the acoustic wave pulses belonging to the group just preceding said period.

Unless contrary specified, by "amplitude", it is meant the mathematical function of evolution with respect to time of the value of a variable, e.g. of an acoustic wave.

According to the invention, a pulse is a repetition pattern of an acoustic wave presenting a maximum (i.e. a highest amplitude). In a group of acoustic wave pulses, the pulses are substantially identically repeated at substantially the same frequency of repetition. A group of pulses may thus consist in a periodical repetition of pulses. A pulse may be a portion of a sine curve, triangle-shaped or square-shaped.

The acoustic wave(s) applied during the period(s) may comprise acoustic wave pulses.

In the particular case wherein the modulated pulsed acoustic field applied at step b) comprises a succession of sets of acoustic wave pulses, the pulses present in each of said set having the same amplitude and frequency, the first group of acoustic wave pulses corresponds to the first set of acoustic wave pulses applied to the objects during step b). Thus, in this particular example, the first period separating two groups corresponds to the second set of acoustic wave pulses applied.

The present invention may advantageously allow the obtaining of a more controlled aggregation mechanism.

The present invention may advantageously allow the obtaining of a resultant aggregate whose architecture can be modified irrespective of the initial object concentration.

The present invention may advantageously allow the reduction of the acoustic field generator heating in comparison with the use of continuous ultrasound.

The present invention may advantageously allow the reduction of the liquid/objects media heating thus maintaining constant the thermodynamic and physicochemical properties of the suspension.

The present invention may advantageously allow the obtaining of an increased acoustic force through employment of a minimum number of pulses that results in rapid yet controlled object aggregation without adversely affecting said objects.

The present invention may advantageously allow the selective generation of 2-D or 3-D aggregates.

The formed aggregate of objects may have a size of 1 nm or more, for example 1 µm or more, for example 1 mm or more.

By "size of the aggregate of objects", it is meant its greatest dimension.

The formed aggregate may not settle down during step b).

Modulated Pulsed Acoustic Field

Groups of Acoustic Wave Pulses

In an embodiment of the invention, each of the groups of acoustic wave pulses comprises 10 or more, preferably 25 or more, preferably 50 or more, preferably 100 or more, acoustic wave pulses.

In an embodiment of the invention, at least one, preferably at least 25%, preferably at least 50%, preferably at least 75%, preferably the totality, of the groups of acoustic wave pulses lasts a duration $t_1$ that is greater than or equal to 0.01 ms, preferably to 0.025 ms.

Step b) may comprise submitting the objects to at least 100, for example 500, for example 1000, for example 5000, for example 10000, for example 25000; for example 50000, groups of acoustic wave pulses.

The highest amplitude of pulses in all or part of the groups is preferably greater than the temporal average of the absolute value of the amplitude of the acoustic wave(s) applied during the period(s).

The temporal average of the absolute value of the amplitude of the acoustic wave(s) applied during the period(s) may be less than or equal to 50%, preferably less than or equal to 25%, more preferably less than or equal to 1.0%, of the highest amplitude of pulses in the group just preceding the considered period(s).

The highest amplitude of pulses in all or part of the groups may be greater than the highest amplitude of the acoustic wave(s) applied during the period(s).

As detailed below, it is preferable that the groups of acoustic wave pulses are separated during step b) by period (s) wherein no acoustic wave is applied.

The acoustic wave pulses belonging to two successive groups separated by at least one period preferably have substantially the same amplitude and frequency. In other words, the acoustic wave pulses belonging to two different groups applied at step b) preferably have substantially the same amplitude and frequency.

In an embodiment, the groups of acoustic wave pulses are periodically spaced between each other by a period having a non-zero duration.

Period(s) Separating the Groups of Acoustic Wave Pulses

In a preferred embodiment, the groups of acoustic wave pulses are separated between each other by a period having a non-zero duration wherein no acoustic wave is applied.

In a variant, it is also possible that the groups of acoustic wave pulses are separated between each other by a period having a non-zero duration wherein an acoustic wave is applied, e.g. having a highest amplitude that is less than the highest amplitude of the acoustic wave pulses present in the group just preceding said period.

In an embodiment, at least one period, for example at least 25% of the periods, for example at least 50% of the periods, for example at least 75% of the periods, for example the totality of the periods, separating two successive groups of acoustic wave pulses has a duration $t_2$ that is greater than or equal to 0.05 ms, preferably 0.1 ms, more preferably to 0.2 ms.

In an embodiment, at least one period, for example at least 25% of the periods, for example at least 50% of the periods, for example at least 75% of the periods, for example the totality of the periods, separating two successive groups of acoustic wave pulses has a duration $t_2$ that is less than or equal to 0.5 s, preferably to 0.1 s, more preferably to 0.01 s, more preferably to 0.005 s.

Pulse Mode Factor

In an embodiment, at least a couple, for example at least 25% of the couples, for example at least 50% of the couples, for example at least 75% of the couples, for example the totality of the couples, of consecutive group of acoustic wave pulses of duration $t_1$ and period separating two successive groups of acoustic wave pulses of duration $t_2$ has a pulse mode factor $$P_{mf} = \frac{t_1}{t_1 + t_2}$$

that is greater than or equal to 0.01, preferably 0.025, more preferably 0.1.

In an embodiment, at least a couple, for example at least 25% of the couples, for example at least 50% of the couples, for example at least 75% of the couples, for example the totality of the couples, of consecutive group of acoustic wave pulses of duration $t_1$ and period separating two successive groups of acoustic wave pulses of duration $t_2$ has a pulse mode factor $$P_{mf} = \frac{t_1}{t_1 + t_2}$$

that is less than or equal to 0.95, preferably 0.75, more preferably 0.5.

In an embodiment, at least two couples of consecutive group of acoustic wave pulses of duration $t_1$ and period separating two successive groups of acoustic wave pulses of duration $t_2$ have a different pulse mode factor $$P_{mf} = \frac{t_1}{t_1 + t_2}.$$

In an embodiment, all the couples of consecutive group of acoustic wave pulses of duration $t_1$ and period separating two successive groups of acoustic wave pulses of duration $t_2$ have substantially the same pulse mode factor $$P_{mf} = \frac{t_1}{t_1 + t_2}.$$

Of course, the present invention also encompasses embodiments wherein the modulated pulsed acoustic field applied at step b) is modulated in amplitude and in frequency.

Temporal Average Speed of Growth of the Upper and/or Lower Surface Area of the Created Aggregate In an embodiment, the upper and/or lower surface area of the created aggregate has a temporal average speed of growth during step b) that is less than or equal to 0.1 mm$^2$/s, preferably 0.05 mm$^2$/s, more preferably 0.03 mm$^2$/s, more preferably 0.015 mm$^2$/s.

Measurement Protocol

Measurements of the cell and particle aggregate surface areas were carried out using the Cell P (Soft Imaging System; SIS, GmbH) and Image J image processing softwares respectively.

Films at a rate of 24 images/s were recorded, and the surface area of the aggregate was determined using the free-hand software tool; the contour of the aggregate was delineated at different times during the aggregation process and the aggregate surface area (in pixels) was automatically calculated. The normalized aggregate surface area was quantified by dividing the aggregate surface area at specific time points during the aggregation process over the aggregate surface area when the aggregate growth was complete i.e. when no single particles or cells were joining the already formed aggregate (still some particles remained at a distance from the central aggregate without moving or moving at extremely low velocities).

Finally, the temporal average speed of growth of the upper and/or lower surface area was estimated by differentiating the measured normalized aggregate surface area with respect to time for each created aggregate.

Adaptation of the Modulated Pulsed Acoustic Field

In an embodiment, during step b), at least one feature of the aggregate is measured and at least one feature of the modulated pulsed acoustic field is modified in function of this measure.

The measured feature may be the instantaneous temporal speed of growth of the upper and/or lower surface area of the created aggregate.

Acoustic Field Generator and Acoustic Waves

In a preferred embodiment, a standing acoustic wave is created along a transverse dimension, preferably along the thickness, of the channel at step b) during the application of the modulated pulsed acoustic field.

The frequency of the acoustic wave pulses present in all or part of the groups of acoustic wave pulses applied at step b) may be of 10 MHz or less, preferably comprised between 0.5 and 10 MHz.

The use of an acoustic field generator in such ranges of frequency may advantageously facilitate maintenance of the integrity of living cells or objects such as vesicles, liposomes, bacteria or viruses.

The modulated pulsed acoustic field used at step b) may advantageously be generated along a thickness of the channel.

The acoustic field generator may be a piezoelectric, e.g. ceramic.

It is for example possible to use an acoustic field generator sold under the reference PZ26 by the company Ferroperm Piezoceramics, Kvistgard, Denmark.

The acoustic field generator may be digitally or analogically controlled.

The acoustic field generator may be powered by a wave generator for example the model 5062 sold by Tabor electronics, Israel.

The wave emitted by the wave generator may be amplified by an amplifier, such an amplifier is for example the model 9250 sold by Tabor electronics, Israel.

The wave generator may, during step b), generate waves having an amplitude comprised between 0 and 40 Vp-p (Volts peak to peak), e.g. between 0 and 20 Vp-p.

The acoustic energy density generated during all or part of step b) may be comprised between 1 and 1000 J/m$^3$ (Joules/m$^3$), for example between 1 and 300 J/m$^3$, for example between 5 and 50 J/m$^3$, and may for instance be of 10 J/m$^3$.

The frequency of the acoustic wave pulses present in all or part of the groups of acoustic wave pulses applied at step b) may be a resonant frequency of the channel along one of its transverse dimensions.

The transverse dimensions of the channel are the thickness and the width of the channel.

By "main frequency which is a resonant frequency of the channel along one of its transverse dimensions", it is meant a frequency $f_0$ such that a transverse dimension $\underline{z}$ of the channel, measured at a given position along the longitudinal axis of the channel, satisfies $$z = \frac{n\lambda}{2}$$

where n is an integer, and $$\lambda = \frac{c_f}{f_0}$$

where $c_f$ is the sound velocity in the liquid present in the channel at the temperature of said liquid, for example 20° C.

In other words, the frequency $f_0$ corresponds to the theoretical frequency satisfying, at a given position along the longitudinal axis of the channel, the resonance condition of the acoustic wave in the channel and the formation of a stationary wave along the considered transverse dimension.

The frequency of the acoustic wave pulses present in all or part of the groups of acoustic wave pulses applied at step b) may be comprised between $0.5f_0$ and $1.5f_0$, in particular between $0.75f_0$ and $1.25f_0$.

The acoustic field generator may be fastened to one of the walls of the channel. This fastening may be done using any means known to the skilled artisan as appropriate, in particular by gluing.

A layer of an acoustic adaptation material may be present between the acoustic field generator and at least one of the walls of the channel.

The acoustic adaptation may be made by the use of any appropriate material known to the skilled artisan.

A plurality of acoustic field generators may be present along the length of the channel for generating said modulated pulsed acoustic field at step b), the acoustic field generators preferably being present on the same side of the channel.

In a variant, the acoustic field generators are present at opposite sides of the channel.

Channel

According to the present invention, it is possible to use channels that are described in US 2008/0067128, the content of which is hereby incorporated by reference.

Geometric Features

The width and/or thickness of the channel may vary, optionally decrease, on at least a portion of its length.

Thus, when moving along the longitudinal axis of the channel, the thickness of said channel may be constant or may vary. The channel may in particular comprise at least two zones that axially follow one another and that present different thicknesses.

The channel may present, on at least a portion of its length, in particular on the totality of its length, a thickness that is less than or equal to 3 cm, better less than or equal to 1 cm. The channel is, for example, a micro-channel.

By "micro-channel", it is meant a channel having, over the totality of its length, a thickness that is less than or equal to 1 mm.

The channel may present on at least a portion of its length, in particular over the totality of its length, a thickness comprised between 50 µm and 3 mm, preferably between 100 µm and 500 µm.

The width of the channel may, when moving along the longitudinal axis of said channel, be constant or vary. The channel for example presents two zones that axially follow one another and that present different widths.

By "longitudinal axis of the channel", it is meant the line interconnecting the centers of gravity of the cross-sections of the channel. The longitudinal axis of the channel may be straight or curvilinear and may be contained in a plane which can be a plane of symmetry for some or even all of the cross-sections of the channel.

In an embodiment, the channel width may vary and the channel may be of a pyramidal shape when observed from above. In this particular case, the acoustic field generators may be rectangular or not.

In a variant, the channel may, when observed from above, have the shape of circles connected by sub-channels, in particular rectilinear sub-channels.

In the latter configuration, the acoustic field generators may be cylindrical, said configuration in particular enabling the generation of a mosaic of aggregates.

The channel may have over at least a portion of its length, in particular over the totality of its length, a width comprised between 1 mm and 40 mm, preferably between 5 mm and 20 mm.

The length of the channel, measured along its longitudinal axis, is, for example, comprised between 3 mm and 1000 mm, preferably between 10 mm and 500 mm.

The channel for example has a length of 100 mm, a width of 10 mm and a thickness of 0.4 mm.

According to another exemplary embodiment, the length of the channel may be comprised between 10 mm and 1000 mm, the width of the channel may be comprised between 1 mm and 40 mm and the thickness of the channel may be comprised between 0.5 mm and 3 mm.

The channel may comprise a transversal section that is substantially constant when displacing along its longitudinal axis.

The channel may have over at least a portion of its length, in particular over the totality of its length, a rectangular transversal section.

In a variant, the channel may have over at least a portion of its length, in particular over the totality of its length, a square or circular transversal section.

The channel may advantageously have, over at least a portion of its length, a ratio of width/thickness and/or length/thickness that is greater than or equal to 10.

Such ratios may advantageously prevent three-dimensional effects in the flow profile.

In a preferred embodiment, the channel has, over at least a portion of its length, in particular over the totality of its length, a rectangular transversal section and a ratio width/thickness $\geq 10$.

Walls of the channel may be platelet-shaped.

Walls of the channel may have over at least part, in particular the totality, of their length a thickness comprised between 0.5 mm and 5 mm.

The channel may comprise, over at least a portion of its length, a wall whose thickness varies.

The wall opposite to the wall wherein the acoustic field is generated may freely oscillate when the method according to the invention is carried out.

Inlet(s) and Outlet(s)

The channel may be in fluidic communication with at least one inlet.

The channel may be in fluidic communication with at least one outlet.

The channel comprising an inlet and/or outlet may be placed in a stable frame. The channel inlet(s) and/or outlet(s) may be connected to syringe pumps and/or peristaltic pumps. When they are connected to peristaltic pumps, a hydrodynamic dampener may be added between the peristaltic pump and the channel inlet(s) and/or outlet(s).

The channel may be in fluidic communication with one or more outlet(s) where aggregates, formed by the method according to the invention, may be evacuated.

As such, it may not be necessary to open the channel in order to collect the formed aggregates.

Preferably, at least one of the inlet(s) presents a width that is not less than the width of the channel and/or presents a section that is substantially rectangular.

At least one inlet may open out into the channel substantially parallel to or perpendicular to the longitudinal axis thereof.

In an embodiment of the invention, at least one feed orifice is in fluidic communication with at least one the inlet(s) via a duct, the duct including in particular a diverging portion that diverges from a tip of the duct; the feed orifice opening out into the duct adjacent to said tip, and in particular perpendicularly to the duct.

This diverging portion of the duct makes it possible to form a sheet of substance starting from a feed point.

In an embodiment of the invention, at least one outlet orifice is in fluidic communication with the outlet(s) of the channel via a duct, the duct includes a portion of section that narrows laterally, in particular a portion converging towards a tip, said portion being triangular in shape when observed from above, for example, the outlet orifice opening out into the duct, e.g. adjacent to the tip, and in particular perpendicularly to the duct.

This converging portion of the duct may serve to avoid formation of a stagnation point at the outlet orifice.

Materials Constituting the Channel

The walls of the channel may comprise, in particular consist of, a material chosen among: organic or mineral glasses, quartz, thermoplastic materials, in particular PMMA or polycarbonate, and metals. More generally, it is possible to use any material having a high acoustic impedance, i.e. at least ten times greater than the acoustic impedance of the fluid.

The channel may be fabricated using conventional fabrication methods of the kind used in the field of microfluidics.

Where appropriate, the microchannel may be provided with at least one valve, e.g. a solenoid valve.

Liquid and Objects

The liquid may be a biological liquid such as blood.

In a variant, the liquid may be water.

The liquid may be transparent to visible light.

The liquid may not be flowing during step b).

According to an embodiment, the liquid is flowing during step b), the Reynolds number of the flow of the liquid optionally being less than 10.

The objects may be monodisperse or polydisperse biological cells, in particular blood cells.

The objects may be rigid or deformable particles, for example polystyrene particles.

More generally, the objects may be rigid or deformable particles, polydisperse particles, biological cells, in particular blood cells, e.g. cancer cells in a blood sample, bacteria, colloidal or non-colloidal emulsions, proteins or liposomes.

The objects may be mono or polydisperse biological cells, preferably mammalian tumor or non-tumour cell line, stem cells or primary cell lines.

The average size of objects present in the channel may be less than or equal to 100 µm, better 50 µm, more preferably 25 µm.

By "average size", it is meant the statistical granulometric dimension at the half of the population, known as D50.

The flow rates used may depend on the samples treated, the channel volume and the acoustic forces applied.

For instance, the liquid may be flowing during all or part of the method according to the invention at a flow rate comprised between 0.01 ml/min to 100 ml/min.

In a particular embodiment, the liquid may be flowing at a flow rate of 0.1 ml/min for a channel of volume 1 ml, when the maximum acoustic primary force is of the same order of magnitude as the gravity force, namely 1 pN (pico-Newton=$10^{-9}$) for latex particles or cells of 10 µm diameter.

The volume fraction of objects, measured when said objects are injected in the channel, may be 0.1% (v/v) or more. The volume fraction of objects corresponds to the [(volume of objects)/(volume of liquid containing said objects)]×100%.

BRIEF DESCRIPTION OF THE DRAWINGS

The invention will be better understood from a reading of the detailed description below, of non-limiting examples for its implementation, and from examination of the attached drawings, in which:

FIG. 1 shows a device for carrying out of a method according to the invention,

FIG. 2 shows an aggregate obtained according to a method of the invention,

FIG. 3 is a view according to III-III of the channel used in FIG. 1,

DETAILED DESCRIPTION

Figure 4:
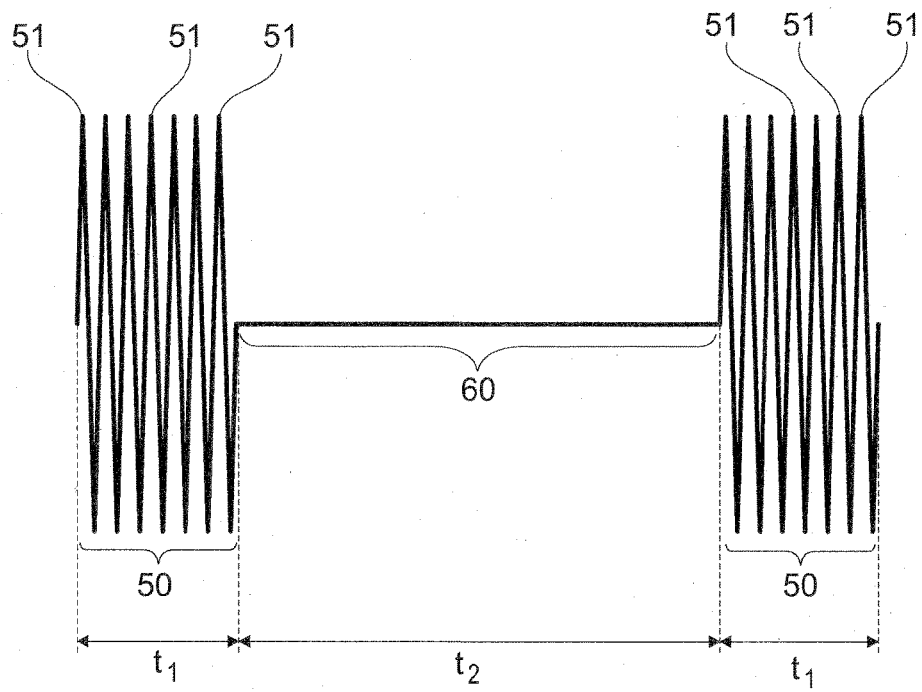
FIGS. 4 and 5 show examples of modulated pulsed acoustic fields for carrying out a method according to the invention.

FIG. 1 shows a device 1 which may be used in the methods according to the invention. The device 1 comprises a channel 2 extending along a longitudinal axis X.

The channel 2 may, as mentioned above, be a microchannel.

The channel 2 may present a cross-section that is rectangular. In the example described, the length/thickness ratio of the channel 2 is greater than 10.

The channel 2 has bottom and top walls 3 and 4. As shown in FIG. 1 for example, a carrier liquid L and a plurality of objects O are present in the channel 2.

Objects O may be mono or polydisperse, said objects O may be biological cells and liquid L may be a biological liquid such as, e.g. blood.

The injection of objects O in the channel 2 can be controlled in frequency and in flow rate so as to enable the device 1 to operate continuously in order to process large volumes of objects.

The device 1 is further provided with an acoustic field generator 10 which is, as shown, fastened to the top wall 4 of the channel 2. The acoustic field generator 10 enables formation, at step b), of an aggregate 20 of objects O by submitting them to a pulsed acoustic field modulated in amplitude. The formed aggregate 20 has as shown in FIG. 3 upper and lower surfaces $S_u$ and $S_l$.

As shown in FIG. 1, the aggregate 20 is in levitation around the pressure node of the waves generated by the acoustic field generator 10. The modulated pulsed acoustic field produced by the acoustic field generator 10 may allow the formation of a standing acoustic wave along the thickness of the channel 2 (Z-axis). The aggregate 20 is as shown in FIG. 1 not in contact with the walls 3 and 4 during step b).

The expression "acoustic levitation" is employed when acoustic manipulation seeks to place objects in an equilibrium position against gravity. The equilibrium position depends on the acoustic properties of the objects and the suspending liquid, the acoustic power and the position and number of nodes of the acoustic waves.

The acoustic field generator 10 may be supplied by a signal from a generator D which e.g. comprise a wave generator connected to an amplifier. The generator D may supply the acoustic field generator 10 with groups of sine-shaped voltage pulses. In a variant, the acoustic field generator 10 may be supplied by the generator D with groups of triangular-shaped or square-shaped voltage pulses.

As explained above, an aggregate of objects may be more compact than a layer of objects. FIG. 2 shows an upper view of an aggregate 20 obtained at the end of step b) according to the invention. The aggregate 20 comprises a set of objects O that are in contact with each other, e.g. at least 50% of the objects O constituting said aggregate 20 can be in contact with each other.

The invention may enable the formation of 2D and/or 3D aggregates. The definition of such 2D and 3D aggregates is given below.

The aggregate 20 comprises a succession $20_1$ of objects O when moving along the Y axis which corresponds to a displacement along the width of the channel 2 but has a thickness formed of at least one object. In this case, the aggregate 20 is a 2D-aggregate.

In an embodiment, the aggregate also comprises a succession of objects O when moving along the thickness of the channel 2. The aggregate is thus a 3D-aggregate.

As shown in FIG. 3, a layer of a gel 11 acting as an acoustic impedance adapter may be present between the acoustic field generator 10 and the top wall 4 of the channel 2.

FIG. 4 shows an example of a temporal evolution of a signal corresponding to a pulsed acoustic field modulated in amplitude which may be used in step b) according to the invention.

The modulated pulsed acoustic field may as shown comprise a repetition of a plurality of groups 50 of acoustic wave pulses 51, said pulses 51 having, among a given group 50, substantially the same amplitude and frequency, and said groups 50 being separated between each other by a period 60 having a non-zero duration wherein no acoustic wave is applied.

Each of the groups 50 of acoustic wave pulses 51 may comprise 10 or more, preferably 25 or more, preferably 50 or more, preferably 100 or more, acoustic wave pulses 51.

The totality of the groups 50 of acoustic wave pulses 51 may last a duration $t_1$ that is greater than or equal to 0.01 ms, preferably to 0.025 ms.

The totality of the periods 60 separating two successive groups 50 of acoustic wave pulses 51 may have a duration $t_2$ that is greater than or equal to 0.05 ms, preferably 0.1 ms, more preferably to 0.2 ms.

The totality of the periods 60 separating two successive groups 50 of acoustic wave pulses 51 may have a duration $t_2$ that is less than or equal to 0.5 s, preferably to 0.1 s, more preferably to 0.01 s, more preferably to 0.005 s.

The present disclosure also encompasses the use of variants of modulated pulsed acoustic field wherein an acoustic wave is applied during a period separating two groups of pulses.

Figure 5:
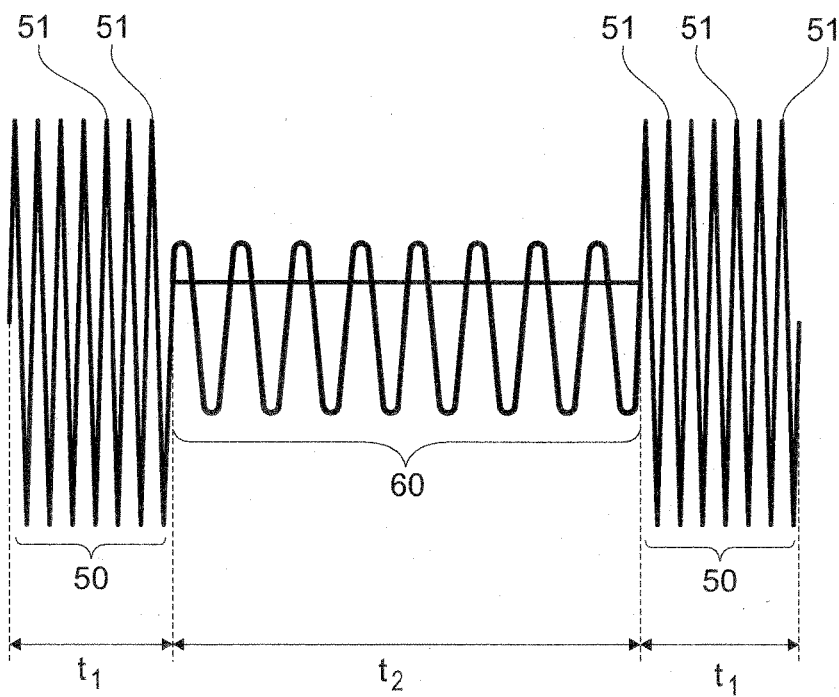

Such an embodiment is shown in FIG. 5 wherein two successive groups 50 of acoustic wave pulses 51 are separated by a period 60 wherein an acoustic wave is applied. The acoustic wave applied during the period 60 has as shown a highest amplitude that is less than the highest amplitude of the acoustic wave pulses 51 of the groups 50.

As shown in FIG. 5, the temporal average of the absolute value of the amplitude of the acoustic wave applied during the period 60, said temporal average corresponding to the horizontal line drawn, is less than 50% and for example approximately equal to 25% of the highest amplitude of pulses 51 in the groups 50.

Figure 6:
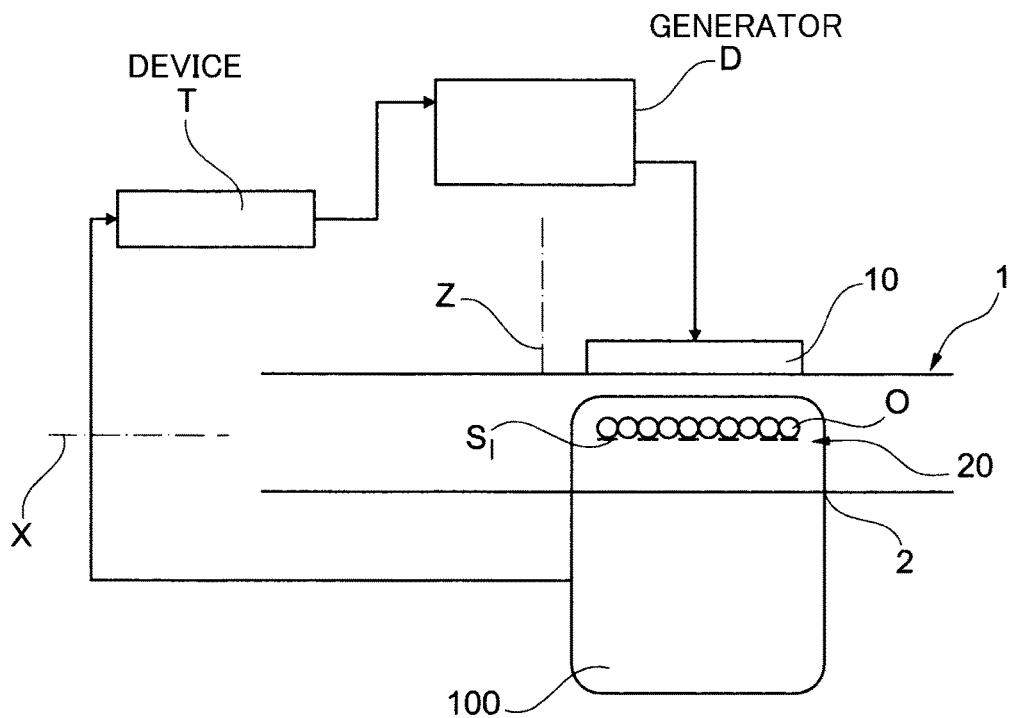
FIGS. 6 to 8 show other embodiments of devices for carrying out of methods according to the invention.

FIG. 6 shows a variant of a device 1 for carrying out a method according to the invention.

In this embodiment, an aggregate 20 is created by submitting objects O to a modulated pulsed acoustic field produced by an acoustic field generator 10.

A device 100 is present and allows the measurement of at least one feature of the aggregate 20. For example, the device 100 may allow the measurement of the instantaneous temporal speed of growth of the lower surface $S_l$ area of the aggregate 20.

Said device e.g. comprises a microscope which allow image capturing in the direction of sound propagation (negative z-axis) connected to a standard PC which is equipped with any suitable software allowing the estimation of the instantaneous temporal speed of growth of the lower surface $S_l$ area of the aggregate 20 (e.g. Cell-D image acquisition and processing software (Soft Imaging System, SIS, GmbH) or Image J software).

This measured feature is then transmitted to a device T controlling the modification of at least one feature of the modulated pulsed acoustic field in function of said measured feature. The device T e.g. controls the modification of the amplitude and/or frequency of the pulses in the groups and/or duration of the periods separating two successive groups.

EXAMPLES

Materials and Methods
Ultrasound Trap

Figures 7A, 7B:
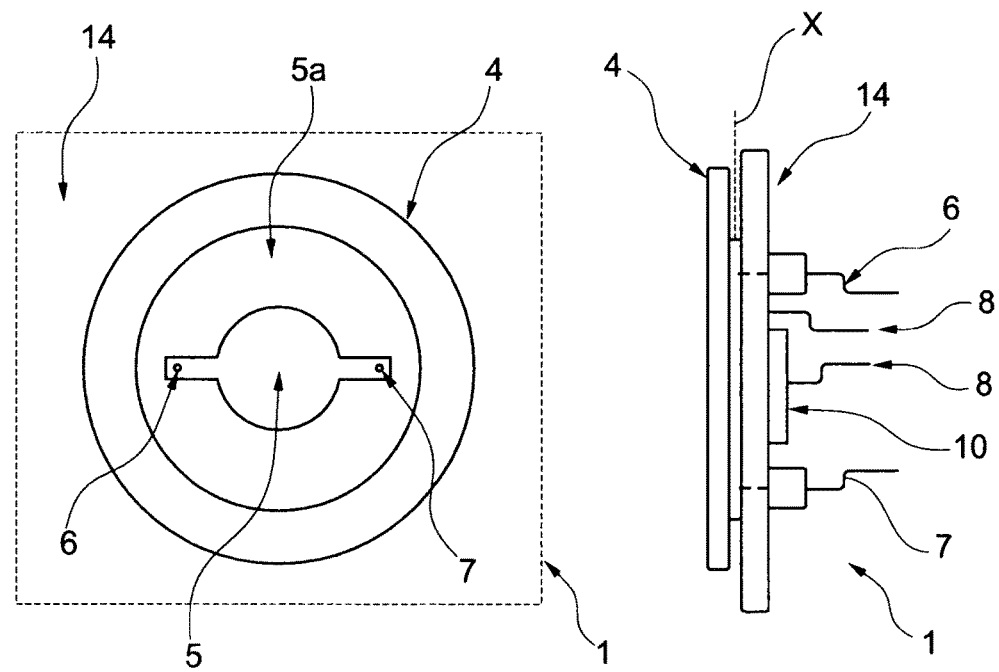
Figure 7C:
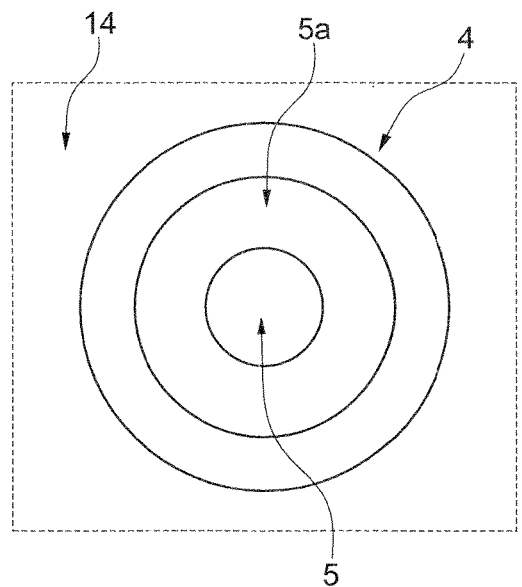

The in-house constructed traps 1 employed are shown in FIGS. 7A (top view of the first trap employed), 7B (side view of the device of FIG. 7A), 7C (top view of the second trap employed) and 7D (side view of the device of FIG. 7C).

These traps have four layers; a transducer 10 (PZ26 Ferroperm, Kvistgard, Denmark) nominally resonant in the thickness mode at 3 MHz and mounted in a radially symmetric housing, a steel layer 14 coupling the ultrasound to a one half wavelength ($\lambda/2$ or 0.25 mm depth, where $\lambda$ is the wavelength of sound in water at 3 MHz) aqueous layer and an acoustic reflector 4, e.g. made of quartz, that provided optical access from above.

A resonant cavity 5 is defined by a polyethylene terephtalate (Mylar®) or polyimide spacer 5a.

It is also possible to use an acoustic reflector made of a plastic material and/or to substitute the steel layer 14 by a layer made of quartz or a plastic material.

The size of the cylindrical steel body was 35 mm. The resonant cavity 5 may have a diameter comprised between 1 mm and 20 mm. The disc transducer (12 mm diameter) 10 was driven at 2.13 MHz.

The trap 1 shown in FIGS. 7A and 7B has one sample inlet 6 and one sample outlet 7. The traps 1 are further provided with connectors 8 for connection to a voltage generator. Each of the connectors 8 is electrically connected to a face of transducer 10. One of the connectors 8 is as shown in contact with the steel layer 14, electrical contact with the face of the transducer 10 fastened to the layer 14 is ensured by a layer of conductive epoxy (not shown).

Figure 7D:
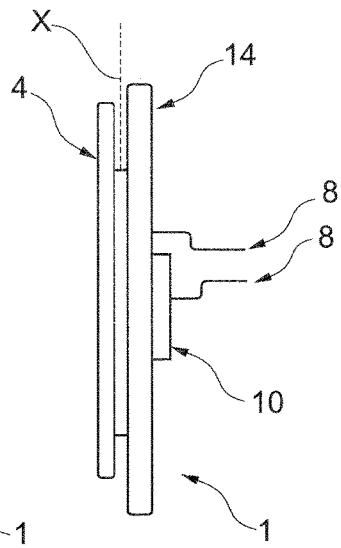

The trap 1 shown in FIGS. 7C and 7D does not comprise any inlet or outlet.

We note that the nominal resonance frequency of the transducer 10 (3 MHz) is different than the nominal resonance frequency of the resonator (2.13 MHz) due to the steel-coupling layer 14. The acoustic reflector 4 may have a thickness of 0.5 mm, 1 mm or 2 mm and may be made of glass, in particular quartz glass.

The piezoceramic transducer 10 was driven by a 100 MHz dual channel arbitrary wave generator (5062 Tabor Electronics, Israel) and the signal was amplified by a dual differential wide band 100 MHz amplifier (9250 Tabor Electronics, Israel). The signal was visualized with a digital storage oscilloscope (IDS 8064 60 MHz ISOTECh, Hanan—Israel).

In experiments with continuous and pulsed ultrasound, amplitudes of 5 to 15 $V_{p-p}$ were employed. Concerning the pulsed acoustic fields used, the number of pulses among each group varied between 25-250 and the repetition frequency of the groups from 1 to 5 kHz.

Optical System

Figure 8:
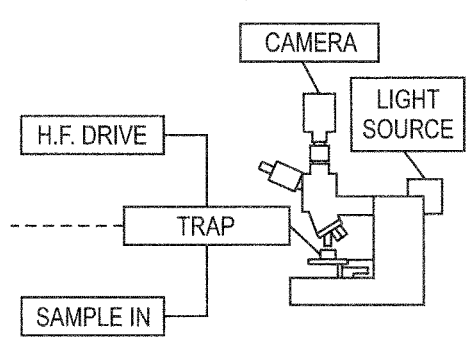

A fast, high-resolution XM10 (Soft Imaging System, SIS, GmbH) mounted on an Olympus BX51M reflection epifluorescence microscope allowed observation in the direction of sound propagation (negative z-axis) (see FIG. 8).

Images were captured by a standard PC equipped with the Cell-D image acquisition and processing software (Soft Imaging System, SIS, GmbH).

Polystyrene Latex Beads Suspensions

We used 15 and 10 μm diameter polystyrene latex particles (density 1,056 kg/m$^3$) supplied as a 10% suspension of solids by Micromod (Rostock, Germany). Aliquots were diluted here to 20 ml to give about 0.15% solids in deionized water.

Cell Culture

Caco2 (human epithelial colorectal adenocarcinoma) cells were obtained from the School of Pharmacy and Pharmaceutical Sciences, Trinity College Dublin, Ireland.

Cells were maintained as a replicative culture at 37° C. under an atmosphere of 95% air and 5% $CO_2$. Caco2 cells were cultured in Modified Eagle Medium (MEM) supplemented with 100 μg/ml penicillin-streptomycin solution, 0.05 g/l sodium pyruvate and 10% foetal calf serum (FCS). At confluence, cells were treated with Trypsin/EDTA solution (1×), for 10 min to release cells from the culture flask surface.

Cells were filtered through a 40 μm Nitex cell strainer (FALCON) to ensure a single cell suspension. Cells were then pelleted by centrifugation at 2000 rpm for 5 min, resuspended in fresh serum-free MEM medium (containing all of the aforementioned supplements), counted and finally diluted to concentrations of 5×10$^5$ cells/ml and 3×10$^6$ cells/ml.

Experimental Procedure

A Gilson minipuls3 peristaltic pump (Gilson, Inc. Middleton, USA) may be used to pump the sample into the ultrasound trap.

The microscope was pre-focused on the central plane of the trap at the axial region. When a pump was used, the pump was switched off and the ultrasound exposure was immediately initiated. The aggregation process was observed using 5×, 10× and 20× objectives.

The pulsed ultrasound approach used consisted in generating groups of pulses (one pulse is one period) at a certain repetition frequency (see e.g. FIG. 4). For instance, at 2 MHz, one pulse lasts for 500 ns; and typically 100 periods may be used, lasting $t_1$=0.05 ms, separated by $t_2$=1 ms repetition time.

This means that for one experiment lasting 1 min, each on-off cycle lasts $t_{cycle}$=1.05 ms, leading to approximately 57,143 on-off cycles during the experiment. The total time at which the force is on will then be ~2.86 seconds, i.e. ~5% of the total time. For the conditions reported above the pulse mode factor $P_{mf}$, defined as $$P_{mf} = \frac{t_1}{t_1 + t_2},$$

is equal to 0.05.

One of the motivations for employing pulsed ultrasound, other than to control the aggregation process, is to avoid transducer heating; a minimum number of pulses fulfill this requirement.

In addition, a minimum number of pulses allow us to increase the acoustic force by increasing the voltage, thereby reducing the risk of transducer damage. In turn, the risk of liquid heating is also reduced, keeping the thermodynamic and physicochemical properties of the suspension as stable as possible.

By using pulsed mode ultrasound it is possible to modify the aggregation velocity by controlling the number of pulses and the repetition frequency. In fact, inventors assume that in continuous mode, particles and cells have the maximum transversal velocity at the nodal plane, while in pulsed mode they slow down in a controlled way.

Experimental Results

The aggregation process starts when isolated particles in levitation converge towards a specific point, where the acoustic energy is maximal.

In the resonator used, levitation of cancer cells was obtained at all frequencies in the range of 2.1 and 2.4 MHz but the optimal aggregation started when the frequency was 2.13 MHz, at which frequency, the aggregation process occurred very fast.

On the other hand, when the frequency was close but not at the optimal resonance frequency, several small aggregates were formed at different positions in the levitation plane. For instance, for cancer cells, operation at the aggregation frequency (2.13 MHz) and at 10Vp-p amplitude, allowed the aggregate to reach its maximum size within 10 s, as we will demonstrate below.

Pulsed Acoustic Field Force

Initially, particles or cells were injected in the resonator where they homogeneously filled the chamber of volume 45 µl. The flow was then stopped, particles settled down and then acoustic field was turned on.

The number of pulses and the repetition frequency were varied while keeping the other parameters constant so as to investigate the effect of a modulated pulsed acoustic field for aggregate formation.

The transducer vibration has the maximum amplitude at the resonance frequency (the transducer vibration amplitude is a few nm and the vibration velocity a few cm/s) but the energy is not uniformly distributed and has a maximum intensity at the center.

The Bernoulli force generated by this effect, as well as by other imperfections of the resonator, acts on particles driving them towards the maximum energy zone, thus leading to the generation of a single aggregate. The fact that in pulsed mode a single aggregate was also observed indicates that the resonance frequency does not change with respect to continuous mode.

In all experiments we aimed at forming aggregates of similar sizes (maximum diameter ~2 mm).

Particle Aggregates

An estimation of the transversal acoustic force responsible for aggregation was made, by measuring (using the software: http://www.cabrillo.edu/~dbrown/tracker/) the migration velocity of a particle at the focusing plane in continuous and in pulsed mode at the resonance frequency of 2.13 MHz.

In continuous mode, single 10 µm and 15 µm latex particles had average transversal velocities of $u_{Tr10}=2\times10^{-5}$ m/s (at 13.8 $V_{p-p}$) and $u_{Tr15}=1.3\times10^{-5}$ m/s (at 16 $V_{p-p}$) respectively. The respective average transversal forces are $F_{Tr}=1.8\times10^{-12}$ N and $2\times10^{-11}$ N; these values are as indicated before, at least two orders of magnitude smaller than the primary radiation force.

Figure 9A:
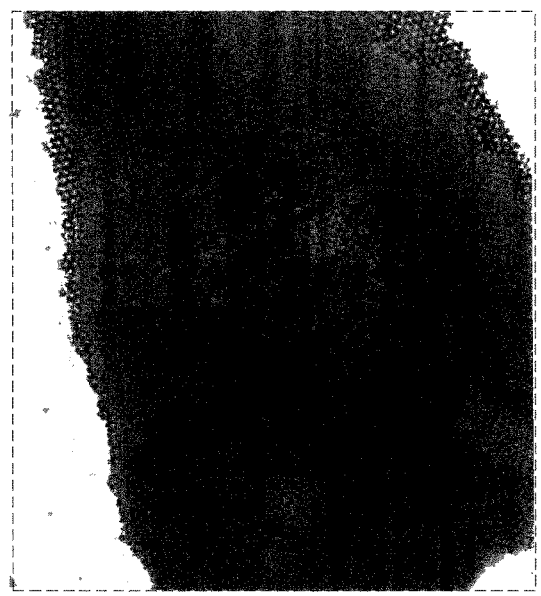
FIG. 9A is a photograph of a 3D aggregate of 15 µm latex particles produced in continuous mode of operation.
Figure 9B:
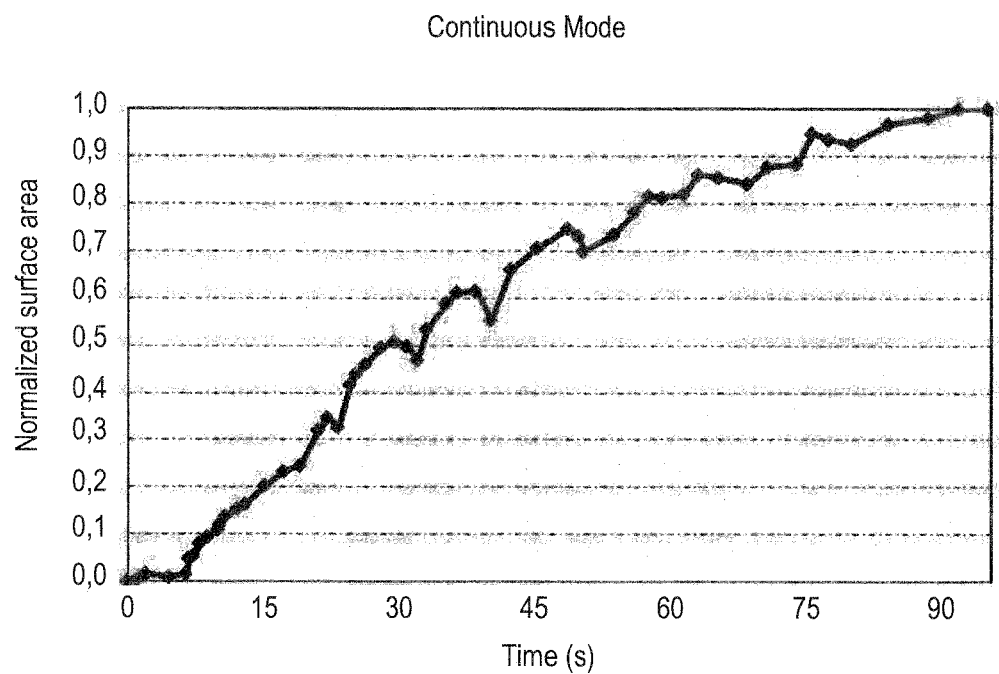
FIG. 9B is a graph showing the evolution of the normalized surface area of the aggregate shown in FIG. 9A.

FIG. 9A shows a 3-D aggregate of 15 µm latex particles formed in continuous mode. The normalized particle aggregate surface area grows monotonically with time showing surface area fluctuations (see FIG. 9B). The aggregation process was completed in 18 s. The voltage used was 16 Vp-p.

Figure 9C:
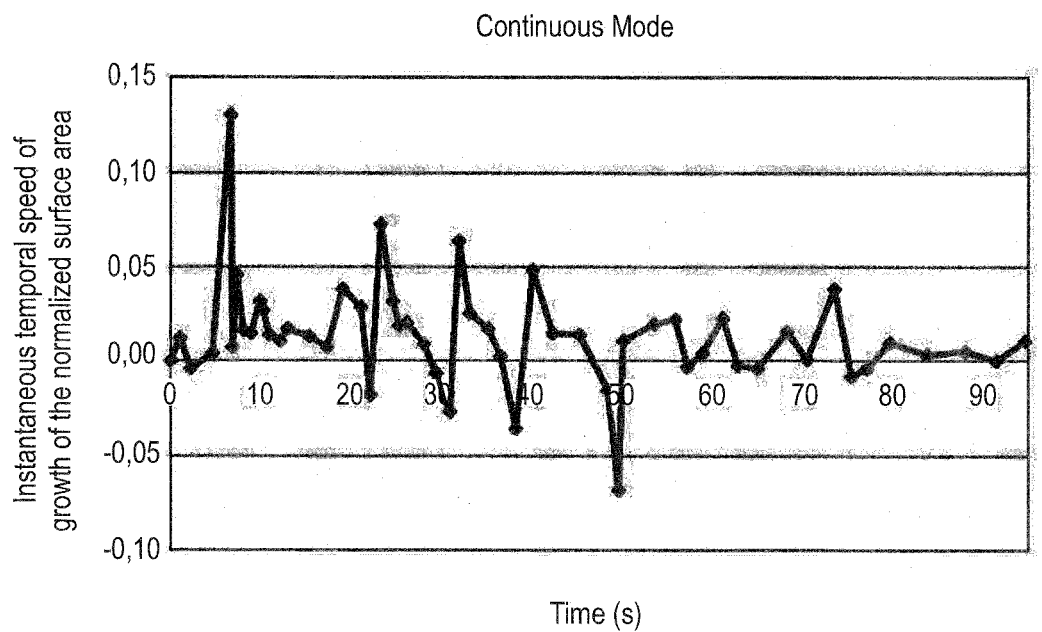
FIG. 9C is a graph showing the evolution of the instantaneous temporal speed of growth of the normalized surface area of the aggregate shown in FIG. 9A.

FIG. 9C (time derivative of the normalized surface area) shows the instantaneous temporal speed of growth of the normalized surface area, the strongest peak appears by 7 s. The resultant aggregate formed is 3-D. The voltage used was 16 Vp-p.

When pulsed ultrasound was employed for 15 µm particles, at 250 pulses and 5 kHz repetition frequency, the average particle velocity was $u_{Tr15\ pulsed}\sim3.5\times10^{-6}$ m/s, corresponding to a transversal acoustic force $F_{Tr}\sim2\times10^{-13}$ N; the latter being much smaller than that obtained in continuous mode. The voltage used was 16 Vp-p.

Figure 10A:
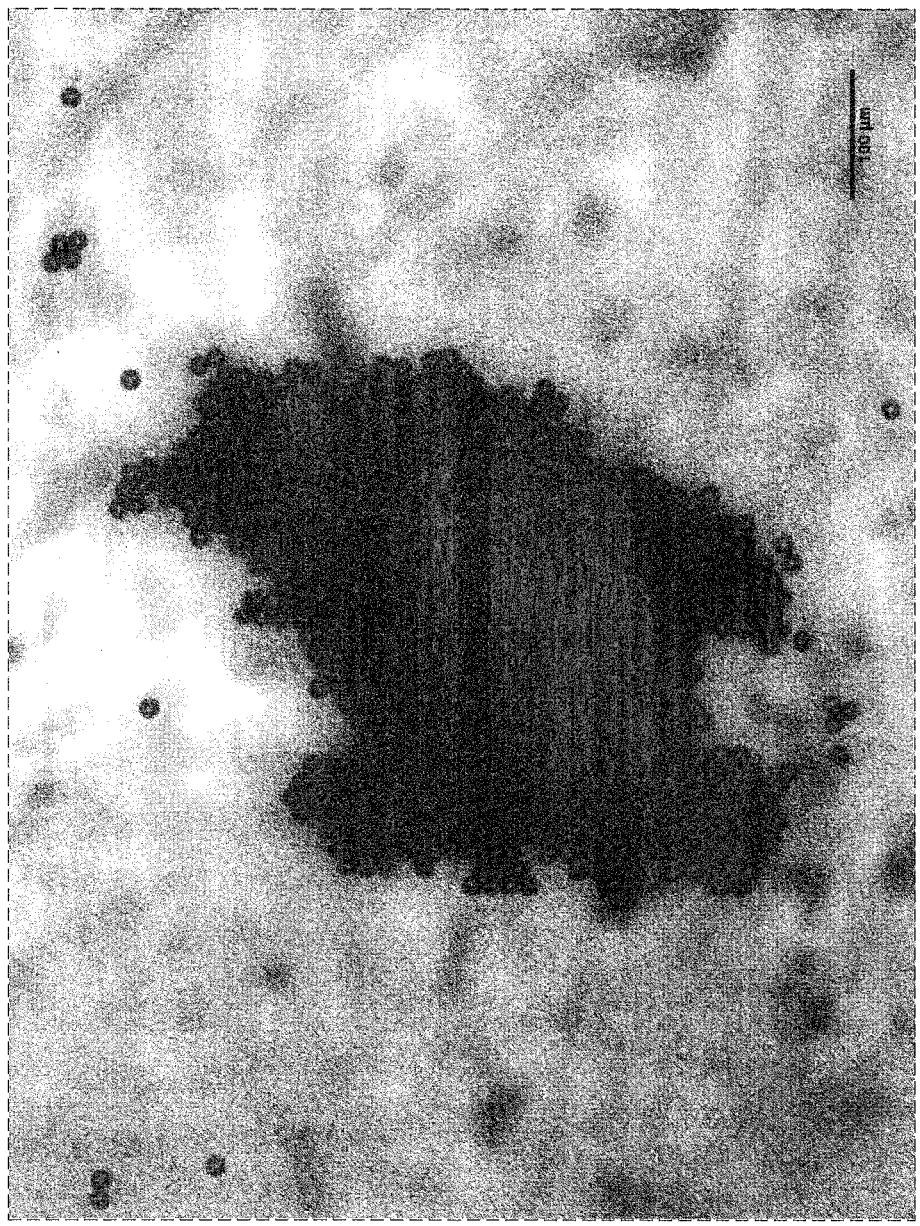
FIG. 10A is a photograph of a 2D aggregate of 15 µm latex particles produced by a pulsed mode method (i.e. using a method according to the invention) at 250 pulses and repetition frequency of 5 kHz.
Figure 10B:
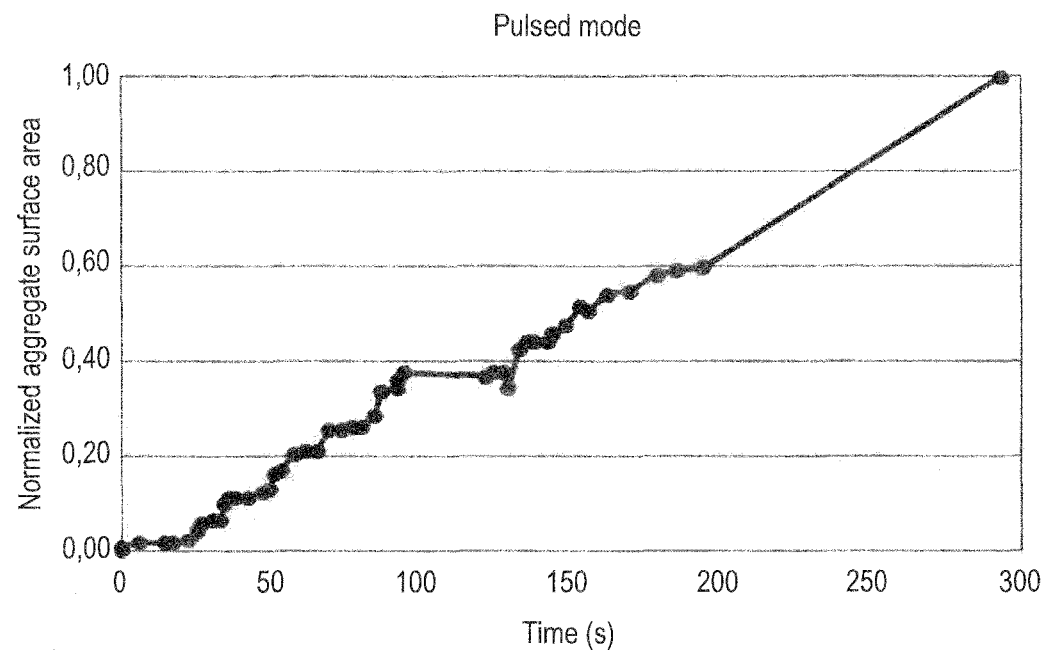
FIG. 10B is a graph showing the evolution of the normalized surface area of the aggregate shown in FIG. 10A.

A 2-D aggregate was formed (see FIG. 10A). The surface area increased linearly with time (see FIG. 10B), and the fluctuations were much smaller than those observed in continuous mode. The instantaneous temporal speed of growth of the normalized surface area of the aggregate shows very small fluctuations (close to zero) (see FIG. 10C).

3-D and 2-D aggregates of 10 µm latex particles, in continuous mode and in pulsed mode at 100 pulses and 4 kHz repetition frequency were also generated. The voltage used in these experiments was 13.8 Vp-p.

The particle velocity in pulsed mode was of the order of $u_{Tr10\ pulsed}\sim4\times10^{-6}$ m/s, much smaller than in continuous mode, corresponding to a transversal force $F_{Tr}\sim4\times10^{-13}$ N.

Figure 11A:
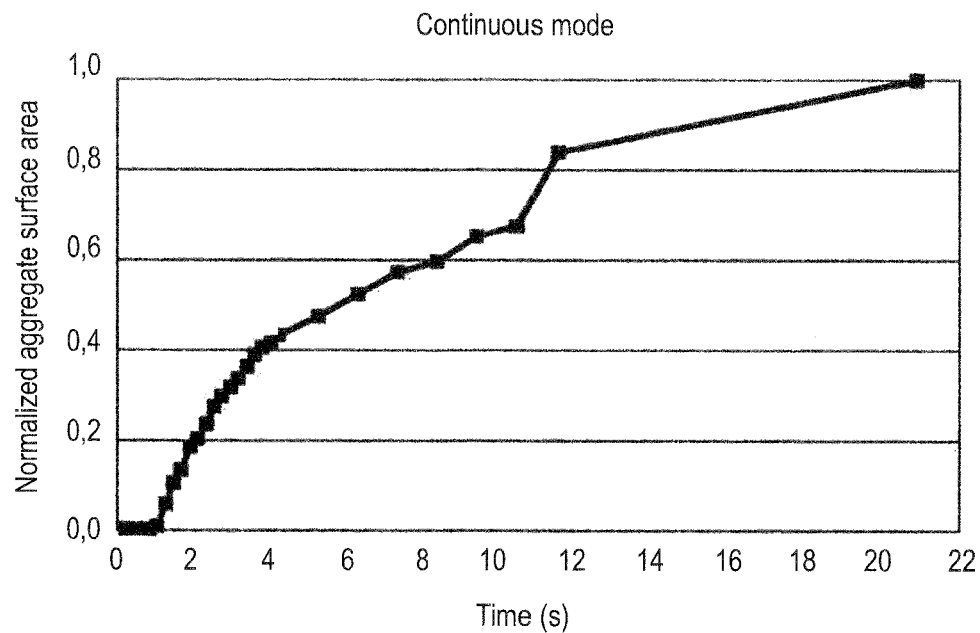
FIG. 11A is a graph showing the evolution of the normalized surface area of an aggregate of 10 µm latex particles produced in continuous mode of operation (i.e. submitting objects to only one group of pulses having substantially the same amplitude and frequency)
Figure 11B:
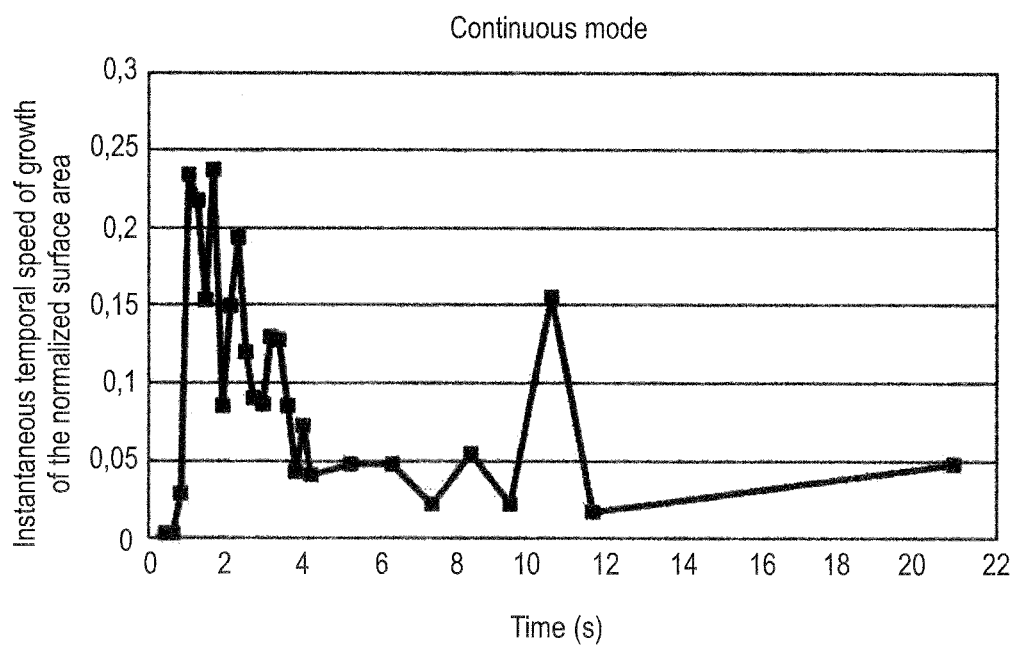
FIG. 11B is a graph showing the evolution of the instantaneous temporal speed of growth of the normalized surface area of an aggregate of 10 µm latex particles produced in continuous mode of operation.

The aggregation in pulsed mode was ended after 300 s when the aggregate was about 2 mm in diameter. FIGS. 11A and 11B show the evolutions of normalized aggregate surface area and of the instantaneous temporal speed of growth of the normalized aggregate surface area.

Features analogous to those of 15 µm particles are observed. Nevertheless, the normalized aggregate surface area growth in continuous mode (see FIG. 11A) showed an initial rapid increase (for the first 4 s), and then decreased to finally becoming linear.

The instantaneous temporal speed of growth of the normalized aggregate surface area, peaked within one second during the aggregation process, followed by a smooth decrease; these features were more pronounced for 10 µm than for 15 µm particles (see FIG. 11B).

Figure 12A:
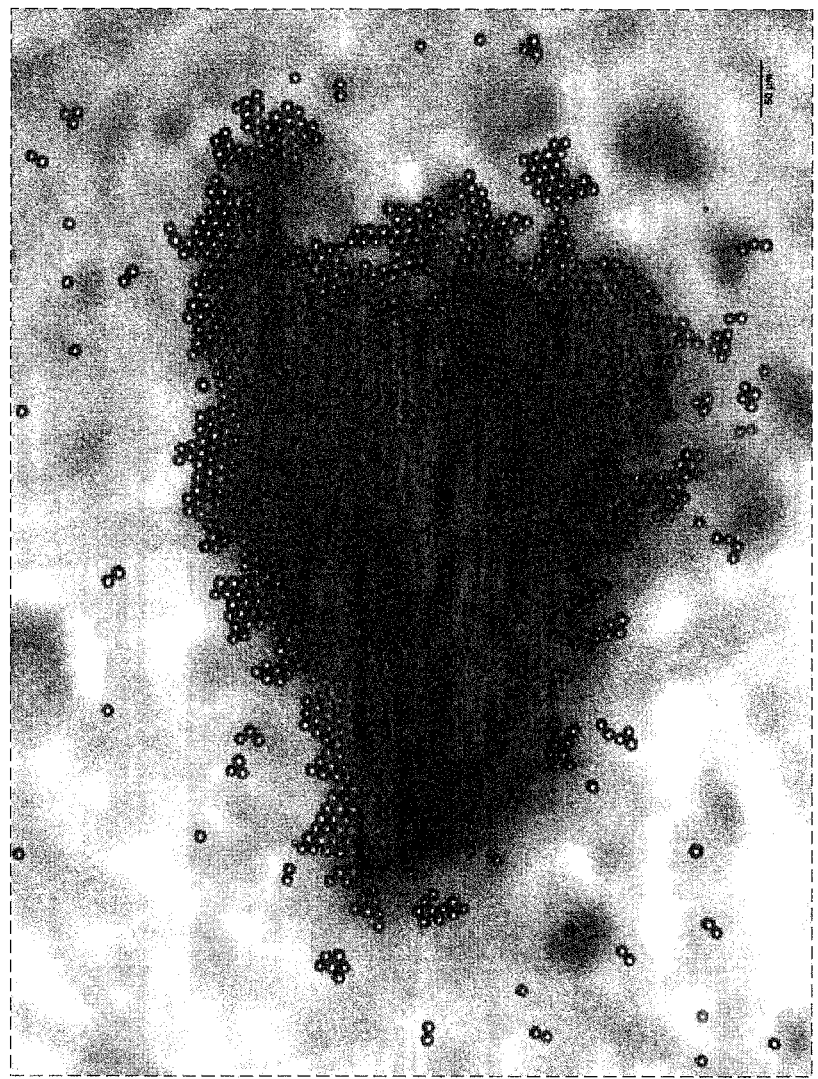
FIG. 12A is a photograph of a 2D aggregate of 10 µm latex particles produced by a method according to the invention (pulsed mode at 100 pulses and repetition frequency of 4 kHz)
Figure 12B:
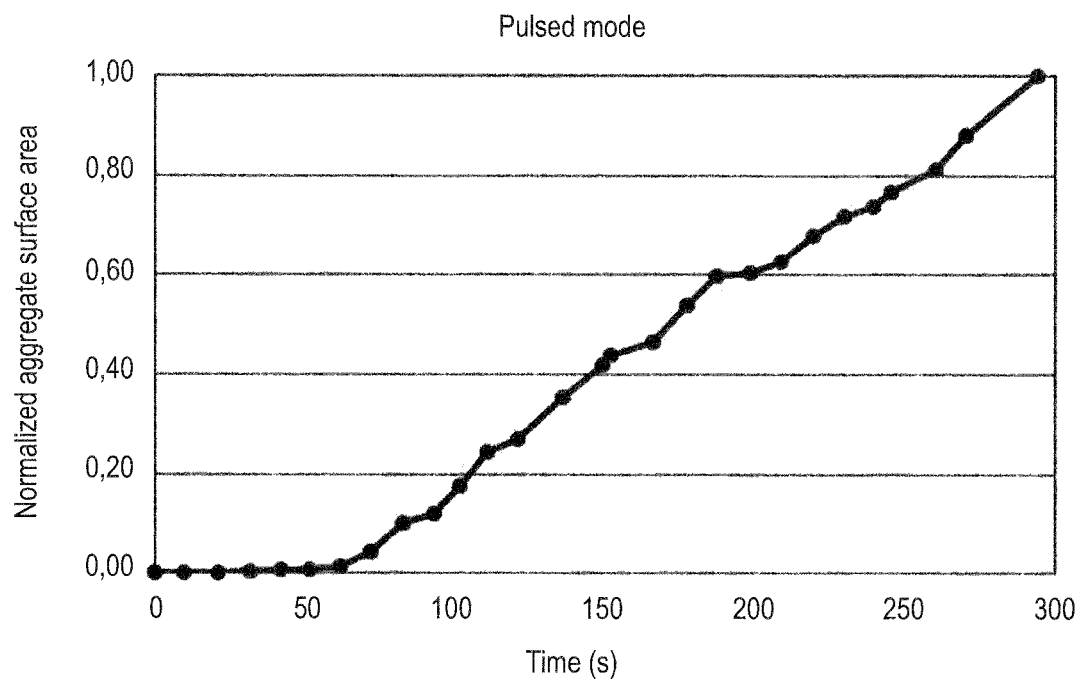
FIG. 12B is a graph showing the evolution of the normalized surface area of the aggregate shown in FIG. 12A.
Figure 12C:
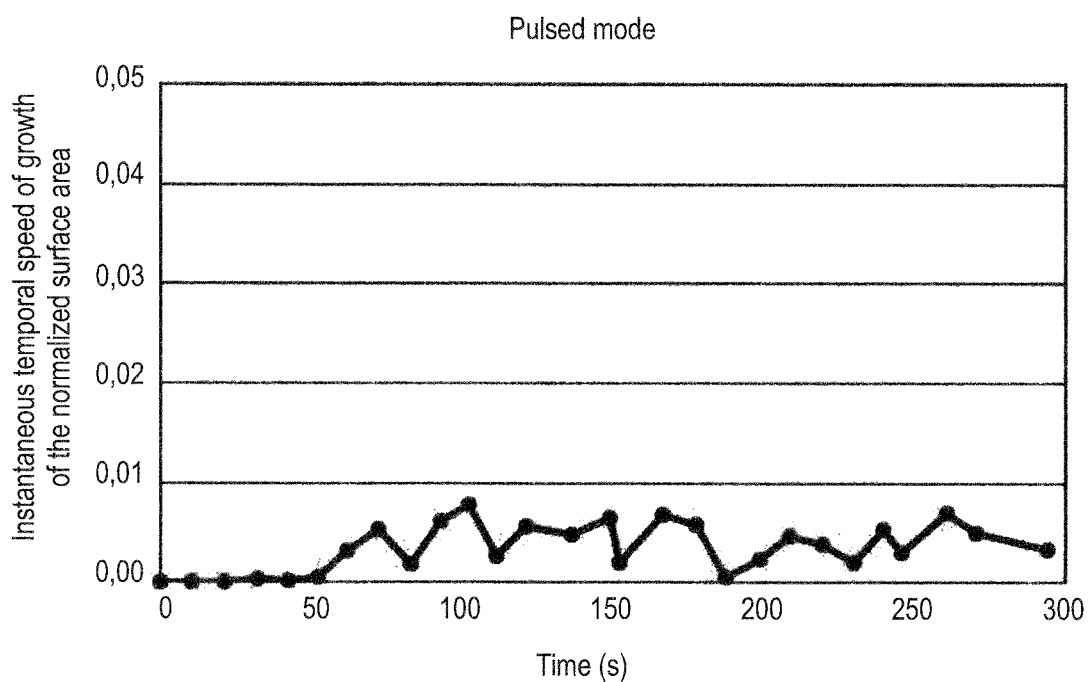
FIG. 12C is a graph showing the evolution of the instantaneous temporal speed of growth of the normalized surface area of the aggregate shown in FIG. 12A, FIGS. 13A and 13B respectively show cell aggregate surface area measurements produced at low ($5\times10^5$ cells/ml) and high ($3\times10^6$ cells/ml) cell concentrations in continuous and pulsed mode (50-200 pulses), FIGS. 14A and 14B respectively show representative Caco2 cell aggregates (concentration $3\times10^6$ cells/ml) produced in continuous and pulsed mode (50 pulses and repetition frequency of 4 kHz), FIGS. 15A and 15B respectively show the evolutions in continuous and pulsed modes of the normalized surface area and of the instantaneous temporal speed of growth of the normalized surface area of an aggregate of Caco2 cells ($3\times10^6$/ml), FIGS. 16A and 16B respectively show 2-D aggregates of 15 μm particles obtained in continuous mode at different voltages: a) 6 Vp-p and b) 4.5 Vp-p.

In pulsed mode, a 2-D aggregate was obtained (see FIG. 12A), the growth of the aggregate surface area was linear (see FIG. 12B) and the instantaneous temporal speeds of growth of the normalized aggregate surface area were negligible compared to those in continuous mode (see FIG. 12C).

Cell Aggregates

For cell aggregation, different experimental parameters were varied including the cell concentration, number of pulses, repetition time and voltage.

The typical cell size was 20 µm and the typical velocities were 223 µm/s in continuous mode and 147 µm/s in pulsed mode, corresponding to acoustic forces of ~12×10$^{-11}$ N and ~5.5×10$^{-11}$ N respectively.

Figure 13A:
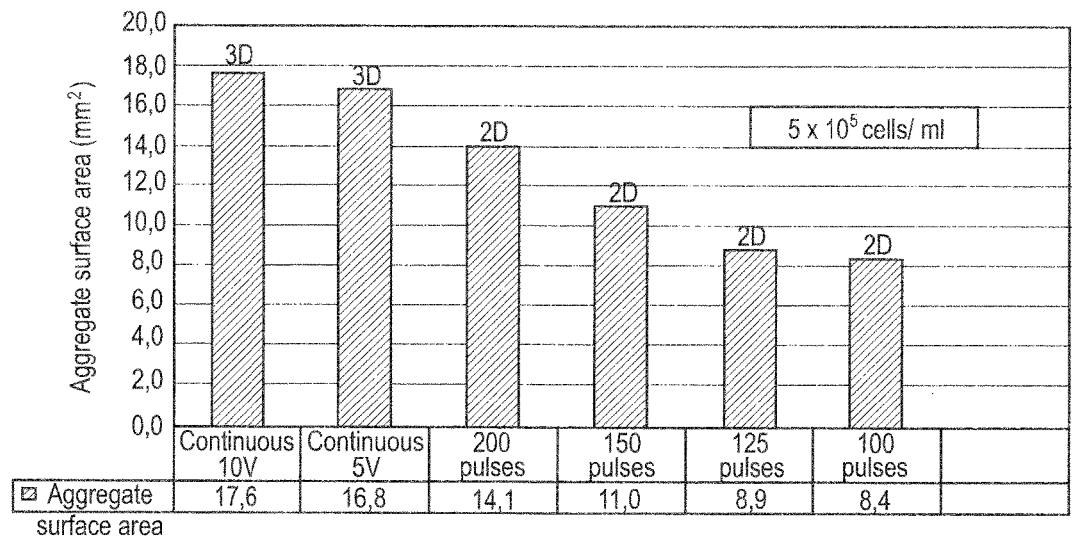
Figure 13B:
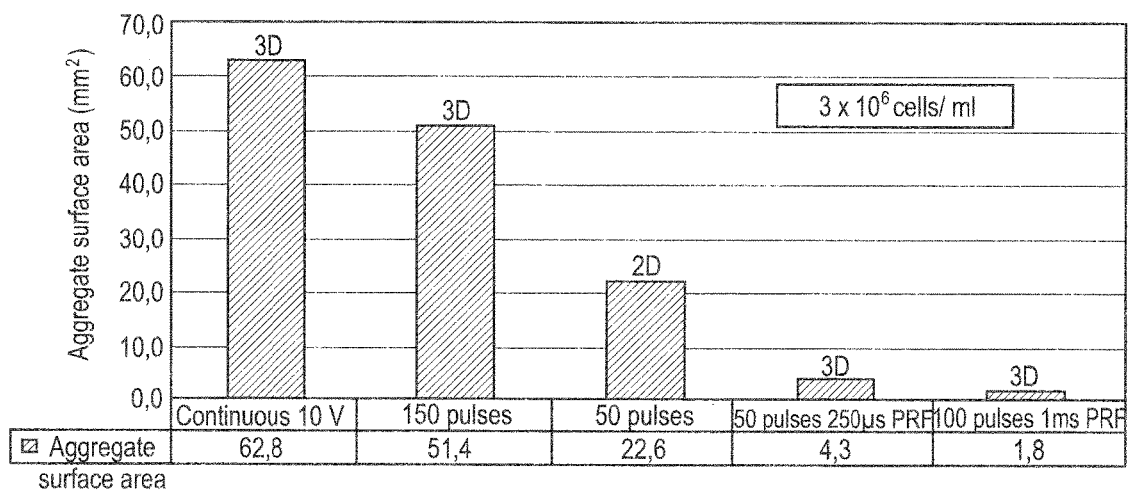

The histograms in FIGS. 13A and 13B show all the parameters and the conditions where 3-D and 2-D aggregates were generated. The voltage used for experiments in pulsed regime was 10 Vp-p. Unless otherwise specified in the figures, the pulse repetition time (period separating two groups of pulses) used in the pulsed mode experiments was 250 µs.

FIGS. 13A and 13B respectively show cell aggregate surface area measurements produced at low (5×10$^5$ cells/ml) and high (3×10$^6$ cells/ml) cell concentrations in continuous and pulsed mode (50-200 pulses). The final cell aggregate architecture (2D or 3D) and the pulse repetition time are also indicated.

Figure 14A:
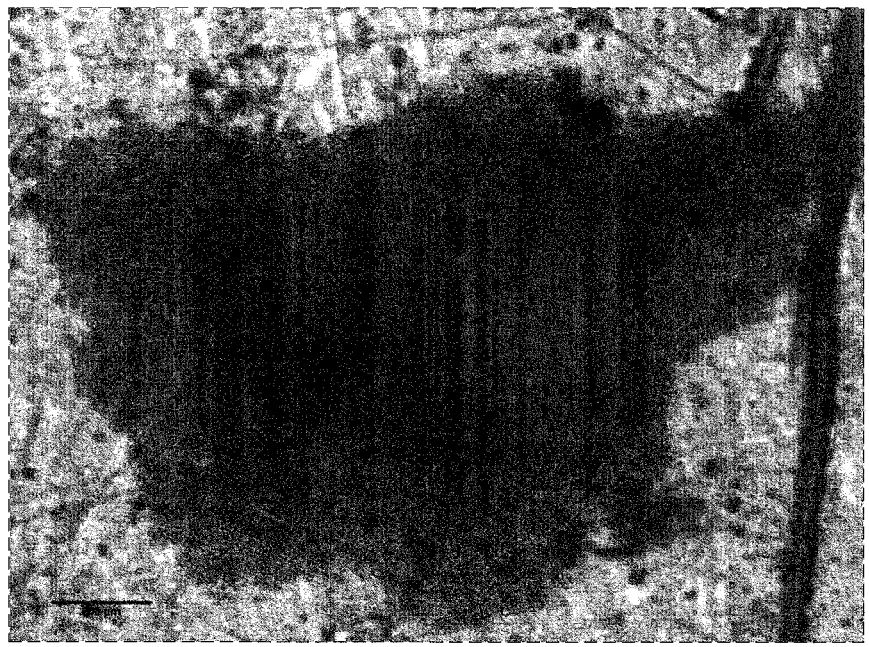
Figure 14B:
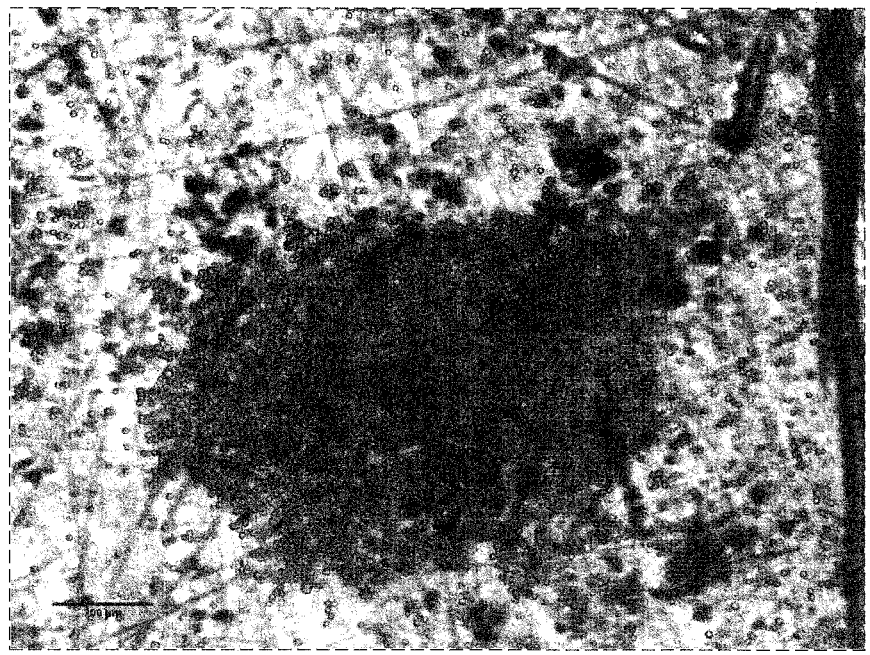

Representative 3-D and 2-D cell aggregates are shown in FIGS. 14A and 14B under continuous and pulsed ultrasound.

Figure 15A:
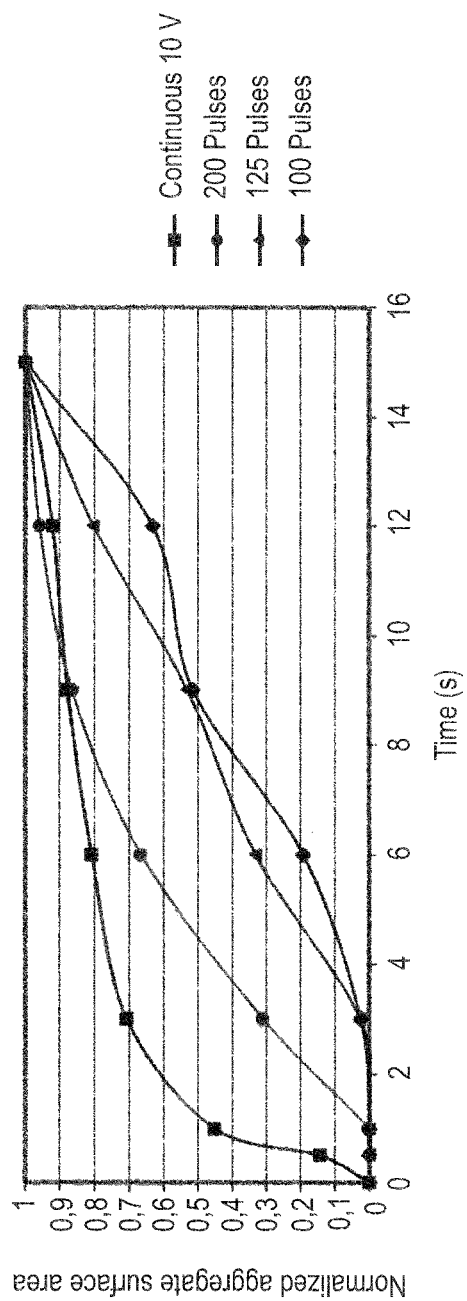
Figure 15B:
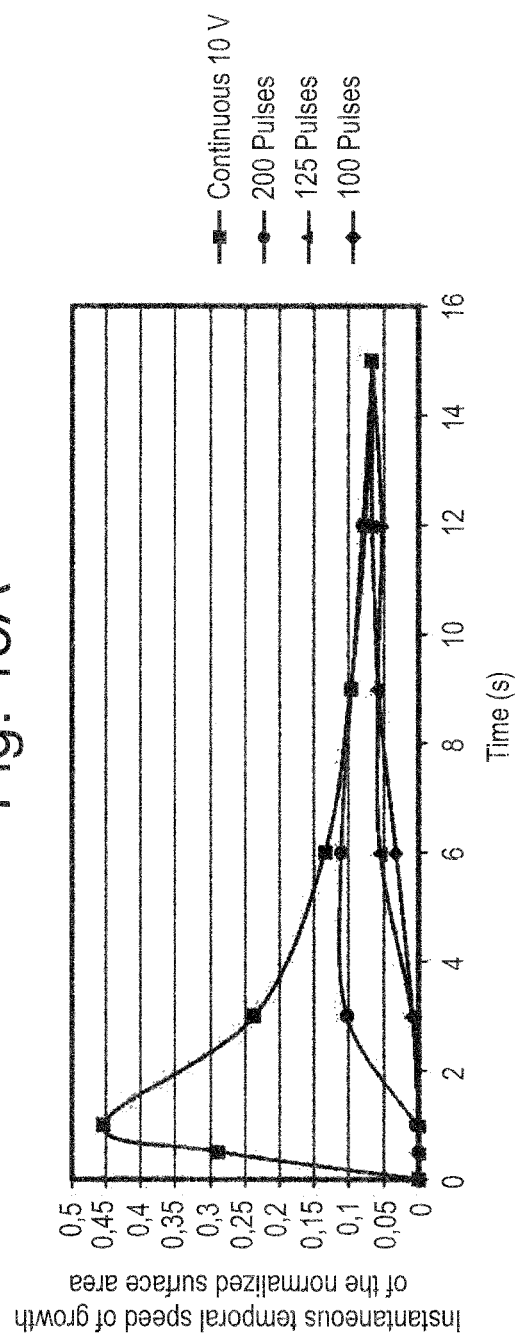

The evolutions of the normalized aggregate surface area and of the instantaneous temporal speed of growth of the normalized aggregate surface area are depicted in FIGS. 15A and 15B respectively. The voltage used was 10 Vp-p.

In continuous mode, the cell normalized aggregate surface area followed the same pattern as that for 10 µm particle aggregates; a rapid increase of the surface area in the first second followed by a linear growth.

In contrast, in pulsed mode the growth was slower and followed a linear pattern. This holds true for all the pulsed ultrasound conditions used here. The speeds of growth in continuous mode showed an initial peak and then decreased to converge with the curves obtained for the different pulsed ultrasound conditions; peaks in pulsed mode curves were rarely observed and were still much smaller than those observed in continuous mode.

Discussion

Initially, we demonstrated how pulsed ultrasound can control particle and cell aggregation. As demonstrated before, the speeds of aggregate growth are reduced when pulsed ultrasound is employed.

The pulse mode factor for 15 and 10 µm particles: $P_{mf15}=0.19$ and $P_{mf10}=0.16$ indicates that the acoustic force was applied during the 19% and 16% of the total experimental time respectively.

By considering that particles have a constant transversal velocity and by taking into account that the drag force is proportional to the velocity, we can compare $P_{mf}$ to the velocity ratio: $u_{pulsed}/u_{continuous}$, being 0.24 for 15 µm and 0.2 for 10 µm particles, not very different from their respective pulsed mode factor.

This result suggests that the inertial effects, i.e. the time needed for reaching the terminal velocity and the relaxation of the maximal amplitude related to the Q-factor, do not significantly influence the aggregation process in pulsed mode.

In the opposite event the values for the Velocity ratio would be smaller than the $P_{mf}$.

The fact that in pulsed mode the aggregation is slower than in continuous mode does not directly imply that lower growth rates entail a higher probability of obtaining 2-D than 3-D aggregates; in fact, the initial particle or cell concentration needs to be taken into consideration.

It is worth noting that in continuous mode during the aggregation process, almost all particles reached the focusing plane before aggregating (only a few particles joined the aggregate from the bottom of the resonator, and their contribution to the 3D structure was negligible), whereas in pulsed mode, all particles started aggregating at the focusing plane.

Our experiments showed that when the aggregate was growing, the momentum transmitted by incoming particles gave rise to the rearrangements of particles and cells, indicating that the pressure distribution in the aggregate was modified.

When the pressure was high enough, particles or layers started to overlap, mostly in the central part of the aggregate, leading to surface area growth rate fluctuations as depicted in FIG. 9C and FIG. 12C.

As in those experiments only few particles joined the aggregate from elsewhere other than from the levitation plane, it is possible to conclude that the overlapping of the particle and cell layers were generated by the increasing pressure of incoming particles, thus determining the transition from 2-D to 3-D aggregates.

Figure 10C:
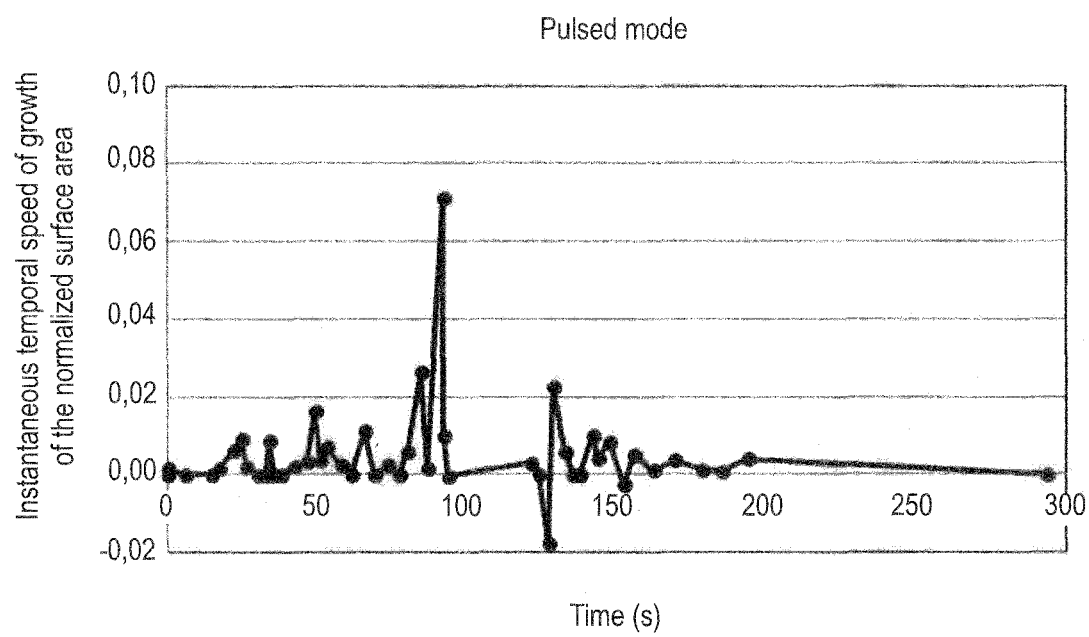
FIG. 10C is a graph showing the evolution of the instantaneous temporal speed of growth of the normalized surface area of the aggregate shown in FIG. 10A.

Experiments with particles clearly showed layer overlapping (see FIG. 9A), while aggregates of cells showed rather darker layers (see FIG. 14A). The aggregation process showed that the fluctuations in the aggregate surface area coincided with the overlapping of layers. These fluctuations disappeared in pulsed ultrasound where only 2-D aggregates were formed. In FIG. 10C (pulsed mode, 15 µm particles), one big fluctuation was observed, but still smaller than those during continuous mode. In fact, in this case we observed, a small aggregate reaching the main aggregate hence generating a great pressure and a strong particle rearrangement; the aggregate was nevertheless 2-D (see FIG. 10A).

This new method is developed with the aim to generate controlled cell constructs.

When cells were employed, even though the surface area fluctuations were visible, the process did not show rapid fluctuations. It is important to note that cells are more elastic than particles, thus initially, compaction of the aggregates occurred with increasing pressure prior to the formation of cell layers.

The curve of the speed of growth of the aggregate surface area in continuous ultrasound is depicted in FIG. 15A. The curve shows a maximum analogous to that shown for 10 µm particles, suggesting that a maximum in the instantaneous temporal speed of growth of the surface area could indicate the formation of a 3D structure. When cells are employed, the aggregate does not grow linearly with time. The elastic properties of the cells as well as their polydispersity could account for this effect.

Finally, the histograms in FIGS. 13A and 13B indicate that the area of the cell aggregates is a function of the number of pulses employed for both concentrations studied.

2D constructs of different sizes can be formed with suspensions of very different initial cell concentrations; for example, 5×10$^5$ cells/ml at 200 pulses generates smaller aggregates than 3×10$^6$ cells/ml at 50 pulses. Regardless of the initial concentration, the pulsed ultrasound technique allows 3D or 2D aggregates to be formed.

Thus, pulsed ultrasound introduces new parameters for controlling the aggregation process.

The possibility of generating 2-D aggregates in continuous mode by reducing the amplitude of the acoustic force, i.e. by reducing the voltage, was investigated. Experiments with 15 µm latex particles (0.1% solids in water) were performed.

Figure 16A:
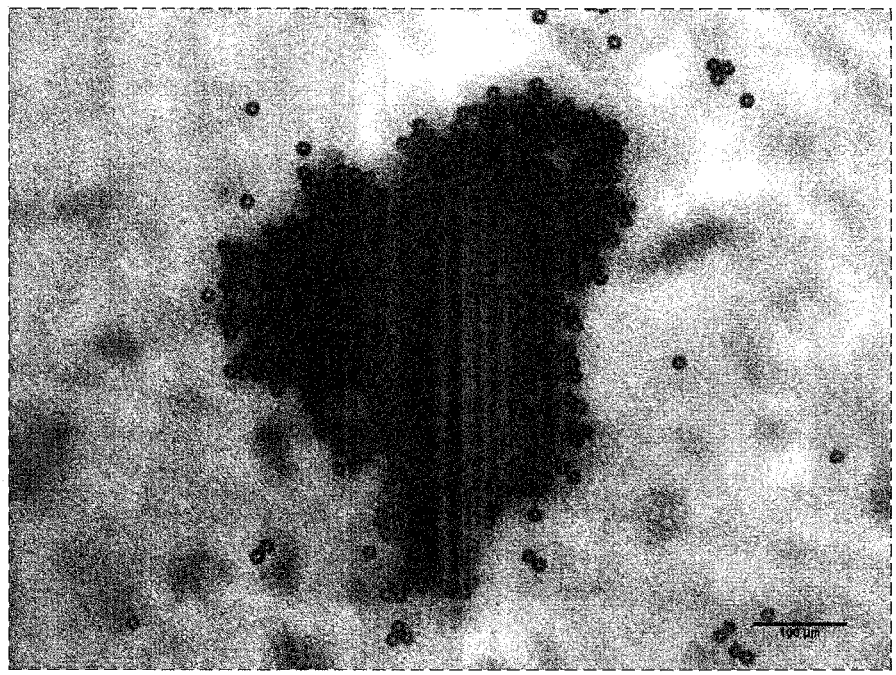
Figure 16B:
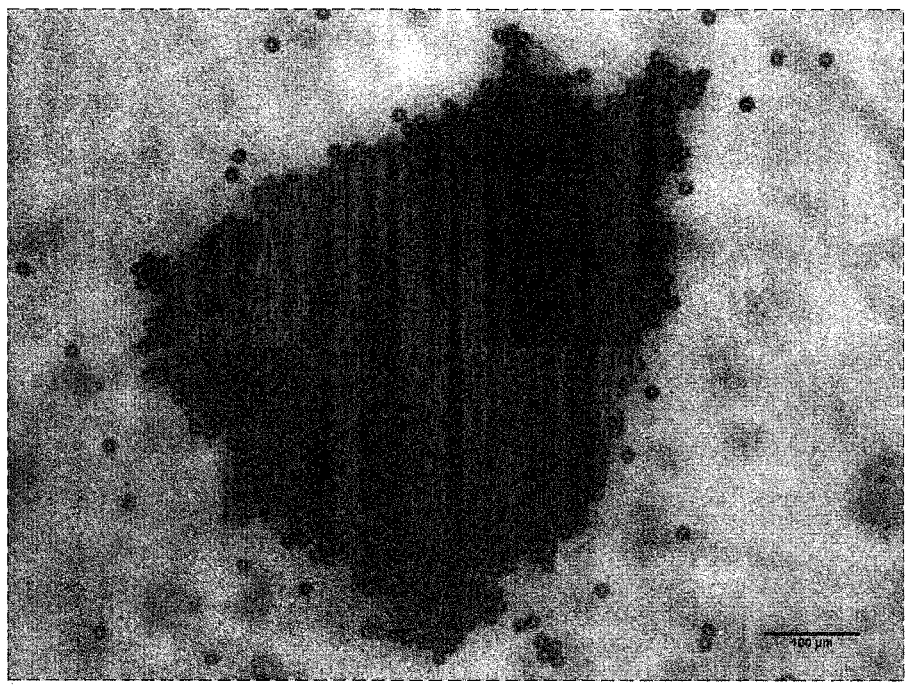

By reducing the voltage to 9 Vp-p, 6 Vp-p and 4.5 Vp-p, an increase in the duration of the aggregation time was observed, as expected. At 9 Vp-p the aggregate was still 3-D. At 6 Vp-p the aggregate was mostly 2-D (see FIG. 16A), as it was difficult to distinguish whether all particles were at the same plane at the centre of the aggregate. At 4.5 Vp-p the aggregate was 2-D but at the center a concave shape showed that the aggregate was not in plane (see FIG. 16B). We also observed that the aggregation time was double the aggregation time in pulsed mode.

At 6 Vp-p and 4.5 Vp-p the aggregate looks like 2-D but, at the centre, particles are unfocused, and the aggregate is not in plane. At higher voltages the aggregate is 3-D.

Finally, by comparing the 2-D aggregates obtained at reduced voltage and in pulsed mode (see FIG. 10A) we can see that in pulsed mode the aggregate is plane and regular.

Based on these observations, it can be considered that when reducing the voltage in continuous mode to control aggregation, it is difficult to get an accurate voltage to generate the optimum or required 2-D aggregate.

The expression "comprising alone" should be understood as "comprising at least one".

The expression "comprised between . . . and . . . " should be understood with the end points included.

The invention claimed is:

1. A method of forming an aggregate of objects in a channel comprising a liquid, said method comprising:
   a) providing objects in at least a region of the channel, and
   b) forming an aggregate of said objects by submitting them to a modulated pulsed acoustic field,
   wherein the modulated pulsed acoustic field applied at step b) is modulated in amplitude.

2. A method according to claim 1, wherein the modulated pulsed acoustic field comprises a repetition of a plurality of groups of acoustic wave pulses, said pulses having, among a given group, the same amplitude and frequency, and said groups being separated between each other by a period having a non-zero duration wherein no acoustic wave is applied.

3. A method according to claim 1, wherein the modulated pulsed acoustic field comprises a repetition of a plurality of groups of acoustic wave pulses, said pulses having, among a given group, the same amplitude and frequency, and said groups being separated between each other by a period having a non-zero duration wherein an acoustic wave is applied, said acoustic wave having at least one extremum of the absolute value of its amplitude that is different from the highest amplitude of the acoustic wave pulses belonging to the group just preceding said period.

4. A method according to claim 1, wherein a standing acoustic wave is created along a transverse dimension of the channel at step b) during the application of the modulated pulsed acoustic field.

5. A method according to claim 4, wherein said transverse dimension is the thickness of the channel.

6. A method according to claim 1, the modulated pulsed acoustic field comprising a repetition of a plurality of groups of acoustic wave pulses, said pulses having, among a given group, the same amplitude and frequency, and each of said groups of acoustic wave pulses comprising 10 or more acoustic wave pulses.

7. A method according to claim 1, the modulated pulsed acoustic field comprising a repetition of a plurality of groups of acoustic wave pulses, said pulses having, among a group, the same amplitude and frequency, at least one group of acoustic wave pulses lasting a duration $t_1$ that is greater than or equal to 0.01 ms.

8. A method according to claim 1, the modulated pulsed acoustic field comprising a repetition of a plurality of groups of acoustic wave pulses, said pulses having, among a given group, the same amplitude and frequency and step b) comprising submitting the objects to at least 100 groups of acoustic wave pulses.

9. A method according to claim 1, the modulated pulsed acoustic field comprising a repetition of a plurality of groups of acoustic wave pulses, said pulses having, among a given group, the same amplitude and frequency and at least one period separating two successive groups of acoustic wave pulses having a duration $t_2$ that is greater than or equal to 0.05 ms.

10. A method according to claim 1, the modulated pulsed acoustic field comprising a repetition of a plurality of groups of acoustic wave pulses, said pulses having, among a given group, the same amplitude and frequency and at least one period separating two successive groups of acoustic wave pulses having a duration $t_2$ that is less than or equal to 0.5 s.

11. A method according to claim 1, the modulated pulsed acoustic field comprising a repetition of a plurality of groups of acoustic wave pulses, said pulses having, among a given group, the same amplitude and frequency and wherein at least a couple of consecutive group of acoustic wave pulses of duration $t_1$ and period separating two successive groups of acoustic wave pulses of duration $t_2$ have a pulse mode factor $$P_{mf} = \frac{t_1}{t_1 + t_2}$$

that is greater than or equal to 0.01.

12. A method according to claim 1, the modulated pulsed acoustic field comprising a repetition of a plurality of groups of acoustic wave pulses, said pulses having, among a given group, the same amplitude and frequency and wherein at least a couple of consecutive group of acoustic wave pulses of duration $t_1$ and period separating two successive groups of acoustic wave pulses of duration $t_2$ have a pulse mode factor $$P_{mf} = \frac{t_1}{t_1 + t_2}$$

that is less than or equal to 0.95.

13. A method according to claim 1, at least two couples of consecutive groups of acoustic wave pulses of duration $t_1$ and period separating two successive groups of acoustic wave pulses of duration $t_2$ having a different pulse mode factor $$P_{mf} = \frac{t_1}{t_1 + t_2}.$$

14. A method according to claim 1, all the couples of consecutive groups of acoustic wave pulses of duration $t_1$ and period separating two successive groups of acoustic wave pulses of duration $t_2$ having substantially the same pulse mode factor $$P_{mf} = \frac{t_1}{t_1 + t_2}.$$

15. A method according to claim 1, the modulated pulsed acoustic field comprising a repetition of a plurality of groups of acoustic wave pulses, said pulses having, among a given group, the same amplitude and frequency and said groups of acoustic wave pulses being periodically spaced between each other by a period having a non-zero duration.

16. A method according to claim 1, wherein the created aggregate is a 2D-aggregate.

17. A method according to claim 1, wherein the channel comprises at least a first and a second wall defining an inner volume wherein said liquid is present and wherein the created aggregate is not in contact with said walls during step b).

18. A method according to claim 1 wherein the channel has, over at least a portion of its length, a ratio width/thickness and/or length/thickness that is greater than or equal to 10.

19. A method according to a claim 1, wherein the upper and/or lower surface of the created aggregate has a temporal average speed of growth during step b) that is less than or equal to 0.1 mm²/s.

20. A method according to claim 1, wherein, during step b), at least one feature of the aggregate is measured and at least one feature of the modulated pulsed acoustic field is modified in function of this measure.

21. A method according to claim 20, the measured feature being the instantaneous temporal speed of growth of the upper and/or lower surface of the created aggregate.

22. A method according to claim 1, wherein the formed aggregate of objects has a size of 1 nm or more.

23. A method according to claim 1, the objects being mono or poly disperse biological cells.

24. A method according to claim 1, the average size of the objects being less than or equal to 100 μm.

25. A method according to claim 1, wherein the Reynolds number of the flow is 10 or less during step b).

26. A method according to claim 1, the liquid not be flowing during step b).

* * * * *